(12) United States Patent
Hoying et al.

(10) Patent No.: US 7,670,665 B2
(45) Date of Patent: *Mar. 2, 2010

(54) TUFTED LAMINATE WEB

(75) Inventors: Jody Lynn Hoying, Maineville, OH (US); John Lee Hammons, Hamilton, OH (US); Susan Nicole Lloyd, Erlanger, KY (US); Robert Haines Turner, Cincinnati, OH (US); John Joseph Curro, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 4 days.

This patent is subject to a terminal disclaimer.

(21) Appl. No.: 11/650,821

(22) Filed: Jan. 8, 2007

(65) Prior Publication Data
US 2007/0116926 A1 May 24, 2007

Related U.S. Application Data

(63) Continuation of application No. 10/737,307, filed on Dec. 16, 2003, now Pat. No. 7,172,801, which is a continuation-in-part of application No. 10/610,299, filed on Jun. 30, 2003, now abandoned, which is a continuation-in-part of application No. 10/435,996, filed on May 12, 2003, now abandoned, which is a continuation-in-part of application No. 10/324,661, filed on Dec. 20, 2002, now abandoned.

(51) Int. Cl.
*B32B 3/10* (2006.01)
*B32B 3/26* (2006.01)
*B32B 3/30* (2006.01)
*B32B 27/12* (2006.01)

(52) U.S. Cl. .................. 428/133; 428/85; 428/86; 428/88; 428/90; 428/91; 428/92; 428/93; 428/137; 428/138; 428/139; 428/172; 442/381; 442/387; 442/389; 442/394; 604/367; 604/378; 604/384

(58) Field of Classification Search ......... 428/132–134, 428/136–139, 152, 167, 172, 85, 86, 90, 428/91, 92, 93, 133, 138; 442/387, 389, 442/394; 604/367, 378, 384
See application file for complete search history.

(56) References Cited

U.S. PATENT DOCUMENTS 2,068,456 A 1/1937 Hooper (Continued)

FOREIGN PATENT DOCUMENTS

DE 43 21 155 1/1995

(Continued)

OTHER PUBLICATIONS

PCT International Search Report dated Jun. 22, 2004.

(Continued)

*Primary Examiner*—Jennifer A Chriss
(74) *Attorney, Agent, or Firm*—Andrew J. Hagerty; Gary J. Foose; Roddy M. Bullock

(57) ABSTRACT

An absorbent article having a topsheet, a backsheet, and an absorbent core disposed between the topsheet and the backsheet. The topsheet has a first side and a second side, the first side being a body-facing side. The topsheet defines a CD-MD plane and includes a fibrous nonwoven web and tufts, the tufts having fibers of the fibrous nonwoven web. The topsheet further includes first, second and third zones, each zone being characterized in a Z-direction by the zone fiber orientation, wherein the first and third zones are displaced relative to each other and each include fibers having portions orientated substantially parallel to said CD-MD plane of the topsheet. The second zone is intermediate and adjacent to the first and third zones, the second zone including substantially reoriented fibers that are substantially vertically oriented with respect to the CD-MD plane of said topsheet.

23 Claims, 10 Drawing Sheets

U.S. PATENT DOCUMENTS

| | | |
|---|---|---|
| 2,275,425 A | 3/1942 | Grabec |
| 2,404,758 A | 7/1946 | Teague et al. |
| 2,633,441 A | 3/1953 | Buttress |
| 2,748,863 A | 6/1956 | Benton |
| 2,924,863 A | 2/1960 | Chavannes |
| 3,073,304 A | 1/1963 | Schaar |
| 3,081,500 A | 3/1963 | Griswold et al. |
| 3,081,512 A | 3/1963 | Griswold |
| 3,097,787 A | 7/1963 | Schur |
| 3,137,893 A | 6/1964 | Gelpke |
| 3,355,974 A | 12/1967 | Carmichael |
| 3,542,634 A | 11/1970 | Such et al. |
| 3,566,726 A | 3/1971 | Politis |
| 3,579,763 A | 5/1971 | Sommer |
| 3,681,182 A | 8/1972 | Kalwaites |
| 3,681,183 A | 8/1972 | Kalwaites |
| 3,684,284 A | 8/1972 | Tranfield |
| 3,718,059 A | 2/1973 | Clayton |
| 3,760,671 A | 9/1973 | Jenkins |
| 3,881,987 A | 5/1975 | Benz |
| 3,949,127 A | 4/1976 | Ostermeier et al. |
| 3,965,906 A | 6/1976 | Karami |
| 3,967,623 A | 7/1976 | Elias et al. |
| 4,035,881 A | 7/1977 | Zocher et al. |
| 4,042,453 A | 8/1977 | Conway |
| 4,135,021 A | 1/1979 | Patchell et al. |
| 4,276,336 A | 6/1981 | Sabee |
| 4,379,799 A | 4/1983 | Holmes |
| 4,397,644 A | 8/1983 | Matthews et al. |
| 4,433,018 A | 2/1984 | Tesch et al. |
| 4,465,726 A | 8/1984 | Holmes |
| 4,469,734 A | 9/1984 | Minto et al. |
| 4,543,154 A * | 9/1985 | Reiter .................. 156/73.1 |
| 4,588,630 A | 5/1986 | Shimalla |
| 4,596,567 A | 6/1986 | Iskra |
| 4,741,941 A | 5/1988 | Englebert et al. |
| 4,758,297 A | 7/1988 | Calligarich |
| 4,781,962 A | 11/1988 | Zamarripa et al. |
| 4,798,604 A | 1/1989 | Carter |
| 4,820,294 A | 4/1989 | Morris |
| 4,840,829 A | 6/1989 | Suzuki et al. |
| 4,859,519 A | 8/1989 | Cabe, Jr. et al. |
| 4,886,632 A | 12/1989 | Van Iten et al. |
| 4,935,087 A | 6/1990 | Gilman |
| 4,953,270 A | 9/1990 | Gilpatrick |
| 5,019,062 A | 5/1991 | Ryan et al. |
| 5,062,418 A | 11/1991 | Dyer |
| 5,144,730 A | 9/1992 | Dilo |
| 5,165,979 A | 11/1992 | Watkins et al. |
| 5,171,238 A | 12/1992 | Kajander |
| 5,188,625 A | 2/1993 | Van Iten et al. |
| 5,223,319 A | 6/1993 | Cotton et al. |
| 5,242,632 A | 9/1993 | Mende |
| 5,383,870 A | 1/1995 | Takai et al. |
| 5,387,209 A | 2/1995 | Yamamoto et al. |
| 5,414,914 A | 5/1995 | Suzuki et al. |
| 5,415,640 A | 5/1995 | Kirby et al. |
| 5,429,854 A | 7/1995 | Currie et al. |
| 5,437,653 A | 8/1995 | Gilman et al. |
| 5,470,326 A | 11/1995 | Dabi et al. |
| 5,508,080 A | 4/1996 | Sorimachi et al. |
| 5,518,801 A | 5/1996 | Chappell et al. |
| 5,533,991 A | 7/1996 | Kirby et al. |
| 5,554,145 A | 9/1996 | Roe |
| 5,560,794 A | 10/1996 | Currie et al. |
| 5,567,501 A | 10/1996 | Srinivasan et al. |
| D375,844 S | 11/1996 | Edwards et al. |
| 5,573,719 A | 11/1996 | Fitting |
| 5,575,874 A | 11/1996 | Griesbach, III et al. |
| 5,580,418 A | 12/1996 | Alikhan |
| 5,599,420 A | 2/1997 | Yeo et al. |
| 5,624,427 A | 4/1997 | Dreier et al. |
| 5,624,729 A | 4/1997 | Cohen et al. |
| 5,626,571 A | 5/1997 | Young et al. |
| 5,628,097 A | 5/1997 | Benson et al. |
| 5,648,142 A | 7/1997 | Phillips |
| 5,650,214 A | 7/1997 | Anderson et al. |
| 5,656,119 A | 8/1997 | Srinivasan et al. |
| 5,658,639 A | 8/1997 | Curro et al. |
| 5,667,619 A | 9/1997 | Alikhan |
| 5,667,625 A | 9/1997 | Alikhan |
| 5,691,035 A | 11/1997 | Chappell et al. |
| 5,700,255 A | 12/1997 | Curro |
| 5,704,101 A | 1/1998 | Majors et al. |
| 5,709,829 A | 1/1998 | Giacometti |
| 5,714,107 A | 2/1998 | Levy et al. |
| 5,723,087 A | 3/1998 | Chappell et al. |
| 5,725,927 A | 3/1998 | Zilg et al. |
| 5,730,738 A | 3/1998 | McFall et al. |
| 5,743,776 A | 4/1998 | Igaue |
| 5,792,404 A | 8/1998 | Cree et al. |
| 5,804,007 A | 9/1998 | Asano |
| 5,804,021 A | 9/1998 | Abuto et al. |
| 5,814,389 A | 9/1998 | Giacometti |
| 5,817,394 A | 10/1998 | Alikhan et al. |
| 5,841,107 A | 11/1998 | Riva |
| 5,858,504 A | 1/1999 | Fitting |
| 5,876,391 A | 3/1999 | Roe et al. |
| 5,879,494 A | 3/1999 | Hoff et al. |
| 5,891,544 A | 4/1999 | Chappell et al. |
| 5,895,623 A | 4/1999 | Trokhan et al. |
| 5,914,084 A | 6/1999 | Benson et al. |
| 5,916,661 A | 6/1999 | Benson et al. |
| 5,925,026 A | 7/1999 | Arteman et al. |
| 5,932,316 A | 8/1999 | Cree et al. |
| 5,964,742 A | 10/1999 | McCormack et al. |
| 5,968,029 A | 10/1999 | Chappell |
| 5,986,167 A | 11/1999 | Arteman et al. |
| 5,993,432 A | 11/1999 | Lodge et al. |
| 6,007,468 A | 12/1999 | Giacometti |
| 6,025,050 A | 2/2000 | Srinivasan et al. |
| 6,027,483 A | 2/2000 | Chappell et al. |
| 6,039,555 A | 3/2000 | Tsuji et al. |
| 6,048,600 A | 4/2000 | Hansson |
| 6,096,016 A | 8/2000 | Tsuji et al. |
| 6,114,263 A | 9/2000 | Benson et al. |
| 6,117,524 A | 9/2000 | Hisanaka et al. |
| 6,120,718 A | 9/2000 | Kotek et al. |
| 6,129,801 A | 10/2000 | Benson et al. |
| 6,155,083 A | 12/2000 | Goeser et al. |
| 6,168,849 B1 | 1/2001 | Braverman et al. |
| 6,176,954 B1 | 1/2001 | Tsuji et al. |
| 6,247,914 B1 | 6/2001 | Lindquist et al. |
| D444,631 S | 7/2001 | Woodbridge et al. |
| 6,264,872 B1 | 7/2001 | Majors et al. |
| 6,287,407 B1 | 9/2001 | Stein et al. |
| 6,323,388 B1 | 11/2001 | Melius et al. |
| 6,383,431 B1 | 5/2002 | Dobrin et al. |
| 6,395,122 B1 | 5/2002 | Hisanaka et al. |
| 6,395,211 B1 | 5/2002 | Dettmer et al. |
| 6,410,823 B1 | 6/2002 | Daley et al. |
| 6,417,426 B1 | 7/2002 | Takai et al. |
| 6,420,625 B1 | 7/2002 | Jones et al. |
| 6,423,884 B1 | 7/2002 | Oehmen |
| 6,451,718 B1 | 9/2002 | Yamada et al. |
| 6,452,064 B1 | 9/2002 | Thoren et al. |
| 6,458,447 B1 | 10/2002 | Cabell |
| 6,486,379 B1 | 11/2002 | Chen et al. |
| D466,702 S | 12/2002 | Carlson et al. |
| 6,506,329 B1 | 1/2003 | Curro et al. |
| 6,537,936 B1 | 3/2003 | Busam et al. |
| 6,570,054 B1 | 5/2003 | Gatto et al. |
| 6,613,028 B1 | 9/2003 | Daley |
| 6,620,485 B1 | 9/2003 | Benson et al. |

| | | | |
|---|---|---|---|
| 6,632,504 | B1 | 10/2003 | Gillespie et al. |
| D481,872 | S | 11/2003 | Hennel et al. |
| 6,647,549 | B2 | 11/2003 | McDevitt et al. |
| 6,669,878 | B2 | 12/2003 | Yamada et al. |
| 6,716,498 | B2 | 4/2004 | Curro et al. |
| 6,726,870 | B1 | 4/2004 | Benson et al. |
| 6,736,916 | B2 | 5/2004 | Steinke et al. |
| 6,793,930 | B2 | 9/2004 | Gatto et al. |
| 6,794,626 | B2 | 9/2004 | Kiermeier et al. |
| 6,808,791 | B2 | 10/2004 | Curro et al. |
| 6,818,802 | B2 | 11/2004 | Takai et al. |
| 6,830,800 | B2 | 12/2004 | Curro et al. |
| 6,837,956 | B2 | 1/2005 | Cowell et al. |
| 6,855,220 | B2 | 2/2005 | Wildeman |
| 6,863,960 | B2 | 3/2005 | Curro et al. |
| 6,872,274 | B2 | 3/2005 | Kauschke et al. |
| 6,878,433 | B2 | 4/2005 | Curro et al. |
| 6,884,494 | B1 | 4/2005 | Curro et al. |
| 7,005,558 | B1 | 2/2006 | Johansson et al. |
| 7,033,645 | B2 | 4/2006 | Gatto et al. |
| 7,037,569 | B2 | 5/2006 | Curro et al. |
| 2002/0029445 | A1 | 3/2002 | Laun et al. |
| 2002/0039867 | A1 | 4/2002 | Curro et al. |
| 2002/0082574 | A1 | 6/2002 | Nakashita |
| 2002/0105110 | A1 | 8/2002 | Dobrin et al. |
| 2002/0119720 | A1 | 8/2002 | Arora et al. |
| 2002/0132544 | A1 | 9/2002 | Takagaki |
| 2002/0165508 | A1 | 11/2002 | Klofta et al. |
| 2003/0021951 | A1 | 1/2003 | Desai et al. |
| 2003/0028165 | A1 | 2/2003 | Curro et al. |
| 2003/0077970 | A1 | 4/2003 | DeLucia |
| 2003/0085213 | A1 | 5/2003 | Burckhardt et al. |
| 2003/0191442 | A1 | 10/2003 | Bewick-Sonntag |
| 2003/0191443 | A1 | 10/2003 | Taylor |
| 2004/0022993 | A1 | 2/2004 | Wildeman |
| 2004/0121686 | A1 | 6/2004 | Wong et al. |
| 2004/0122396 | A1 | 6/2004 | Maldonado et al. |
| 2004/0126531 | A1 | 7/2004 | Harvey et al. |
| 2004/0131820 | A1 | 7/2004 | Turner et al. |
| 2004/0137200 | A1 | 7/2004 | Chhabra et al. |
| 2004/0157036 | A1 | 8/2004 | Provost et al. |
| 2004/0161991 | A1 | 8/2004 | Walton et al. |
| 2004/0229008 | A1 | 11/2004 | Hoying |
| 2004/0242097 | A1 | 12/2004 | Hasenoehrl et al. |
| 2004/0265533 | A1 | 12/2004 | Hoying et al. |
| 2004/0265534 | A1 | 12/2004 | Curro et al. |
| 2005/0064136 | A1 | 3/2005 | Turner et al. |
| 2005/0096614 | A1 | 5/2005 | Perez et al. |
| 2005/0123726 | A1 | 6/2005 | Broering et al. |
| 2005/0281976 | A1 | 12/2005 | Curro et al. |
| 2005/0281978 | A1 | 12/2005 | Cabell |
| 2005/0283129 | A1 | 12/2005 | Hammons et al. |
| 2006/0019056 | A1 | 1/2006 | Turner et al. |
| 2006/0087053 | A1 | 4/2006 | O'Donnell et al. |
| 2006/0286343 | A1 | 12/2006 | Curro et al. |
| 2008/0119807 | A1 | 5/2008 | Curro et al. |

FOREIGN PATENT DOCUMENTS

| | | |
|---|---|---|
| EP | 0 509 012 B1 | 7/1995 |
| EP | 0 955 159 A1 | 11/1999 |
| EP | 0 963 747 A1 | 12/1999 |
| EP | 1 004 412 A1 | 5/2000 |
| FR | 2713083 A1 * | 3/1993 |
| FR | 2 713 083 | 6/1995 |
| JP | S-48-107981 | 12/1973 |
| WO | WO 99/62446 A1 | 12/1999 |
| WO | WO 01/76523 A2 | 10/2001 |
| WO | WO 02/100632 A1 | 12/2002 |
| WO | WO 2005/011936 A1 | 2/2005 |

OTHER PUBLICATIONS

Office Action for U.S. Appl. No. 11/129,877; dated Mar. 30, 2007.
Office Action for U.S. Appl. No. 11/129,877; dated Oct. 2, 2007.
Office Action for U.S. Appl. No. 11/129,877; dated Jan. 23, 2008.
Office Action for U.S. Appl. No. 11/129,877; dated Jun. 12, 2008.
Notice of Allowance for U.S Appl. No. 10/737,306; dated Nov. 29, 2007.
Office Action for U.S. Appl. No. 10/737,306; dated Jul. 16, 2007.
Office Action for U.S. Appl. No. 10/737,306; dated Feb. 3, 2006.
Office Action for U.S. Appl. No. 11/158,165; dated May 16, 2008.
Office Action for U.S. Appl. No. 11/158,165; dated Dec. 7, 2007.
Office Action for U.S. Appl. No. 11/158,165; dated Jul. 3, 2007.
Office Action for U.S. Appl. No. 11/157,770; dated Jun. 2, 2008.
Office Action for U.S. Appl. No. 11/157,770; dated Oct. 1, 2007.
Office Action for U.S. Appl. No. 11/156,020; dated Jul. 10, 2008.
Office Action for U.S. Appl. No. 11/156,020; dated Nov. 27, 2007.
Office Action for U.S. Appl. No. 11/156,020; dated Jun. 20, 2007.
Office Action for U.S. Appl. No. 11/156,020; dated Jan. 12, 2007.
Office Action for U.S. Appl. No. 11/155,805; dated May 16, 2008.
Office Action for U.S. Appl. No. 11/155,805; dated Nov. 27, 2007.
Office Action for U.S. Appl. No. 11/155,805; dated Jun. 19, 2007.
Office Action for U.S. Appl. No. 10/737,235; dated Jun. 12, 2008.
Office Action for U.S. Appl. No. 10/737,235; dated Dec. 12, 2007.
Office Action for U.S. Appl. No. 10/737,235; dated Jul. 26, 2007.
Office Action for U.S. Appl. No. 10/737,235; dated Feb. 6, 2007.
Office Action for U.S. Appl. No. 10/737,235; dated Aug. 8, 2006.
Office Action for U.S. Appl. No. 10/737,235; dated Feb. 3, 2006.
Office Action for U.S. Appl. No. 10/737,235; dated Aug. 24, 2005.
Notice of Allowance for U.S. Appl. No. 10/737,307; dated Sep. 28, 2006.
Office Action for U.S. Appl. No. 10/737,307; dated May 31, 2006.
Office Action for U.S. Appl. No. 10/737,307; dated Oct. 7, 2005.
Notice of Allowance for U.S. Appl. No. 10/980,219; dated May 23, 2007.
Office Action for U.S. Appl. No. 10/980,219; dated Mar. 5, 2007.
Office Action for U.S. Appl. No. 10/980,219; dated Sep. 11, 2006.

Notice of Allowance for U.S. Appl. No. 10/737,430; dated Mar. 18, 2008.
Notice of Allowance for U.S. Appl. No. 10/737,430; dated Oct. 29, 2007.
Office Action for U.S. Appl. No. 10/737,430; dated Jul. 16, 2007.
Office Action for U.S. Appl. No. 10/737,430; dated Jan. 25, 2007.
Office Action for U.S. Appl. No. 10/737,430; dated Aug. 8, 2006.
Office Action for U.S. Appl. No. 10/737,430; dated Feb. 3, 2006.
Office Action for U.S. Appl. No. 10/737,430; dated Aug. 24, 2005.
Office Action for U.S. Appl. No. 10/737,306; dated Jun. 12, 2008.
Office Action for U.S. Appl. No. 10/737,306; dated Jan. 26, 2007.
Office Action for U.S. Appl. No. 10/737,306; dated Aug. 9, 2006.
Office Action for U.S. Appl. No. 10/737,306; dated Aug. 24, 2005.
Office Action for U.S. Appl. No. 12/370,850 dated Jul. 8, 2009; Turner et al.; filed Feb. 13, 2009.
Office Action for U.S. Appl. No. 11/157,770 dated Apr. 28, 2009; Hammons et al.; filed Jun. 21, 2005.
Office Action for U.S. Appl. No. 11/156,020 dated Jul. 8, 2009; Curro et al.; filed Jun. 17, 2005.
Office Action for U.S. Appl. No. 11/156,020 dated Dec. 24, 2008; Curro et al.; filed Jun. 17, 2005.
Answer for U.S. Appl. No. 11/155,805 dated Aug. 6, 2009; Curro et al.; filed Jun. 17, 2005.
Office Action for U.S. Appl. No. 11/155,805 dated Oct. 30, 2008; Curro et al.; filed Jun. 17, 2005.
Office Action for U.S. Appl. No. 10/737,235 dated May 6, 2009; Hoying et al.; filed Dec. 16, 2003.
Office Action for U.S. Appl. No. 10/737,235 dated Nov. 25, 2008; Hoying et al.; filed Dec. 16, 2003.
Office Action for U.S. Appl. No. 12/021,369 dated Jun. 25, 2009; Curro et al.; filed Jan. 29, 2008.

* cited by examiner

TUFTED LAMINATE WEB

CROSS-REFERENCE TO RELATED APPLICATION

This application is a continuation of U.S. application Ser. No. 10/737,307, filed Dec. 16, 2003, now U.S. Pat. No. 7,172,801 which is a continuation-in-part of U.S. application Ser. No. 10/610,299; filed Jun. 30, 2003, now abandoned, and which is a continuation-in-part of U.S. application Ser. No. 10/435,996, filed May 12, 2003 now abandoned, which is a continuation-in-part of U.S. application Ser. No. 10/324,661, filed Dec. 20, 2002, now abandoned.

FIELD OF INVENTION

This invention relates to body facing layers of disposable absorbent articles such as sanitary napkins. In particular, this invention relates to topsheets having improved fluid handling properties.

BACKGROUND OF THE INVENTION

Disposable absorbent articles such as disposable diapers, incontinence products, catamenial products and the like are widely used, and much effort has been made to improve the effectiveness and functionality of these articles. In general such articles have a fluid permeable body-facing layer, often referred to as a topsheet, a fluid impermeable garment-facing layer, often referred to as a backsheet, and an absorbent core sandwiched between the topsheet and the backsheet. Other components, such as acquisition layers, secondary topsheets, and adhesive fasteners are also well known in the art.

Conventional body-facing layers, i.e., topsheets, used in disposable absorbent typically exhibit a tradeoff between improved acquisition of gushes of fluid and improved dryness. For example, topsheets can be made relatively hydrophilic to quickly wet out and acquire gushes of fluid, but this same relative hydrophilicity causes the topsheet to feel wet next to the wearer's skin, i.e., dryness is compromised. Various material and component structures have been proposed in the past to provide for either improved gush acquisition or improved rewet, but the properties have remained linked, one being inversely proportional to the other.

It is known that providing for a certain amount of compression-resistant thickness, or caliper, in a topsheet aids in reducing rewet. For example, three-dimensional formed film topsheets such as those known as DRI-WEAVE® topsheets on ALWAYS® sanitary napkins marketed by The Procter & Gamble Co. are known to provide for low rewet, i.e., better dryness, compared to typical nonwoven topsheets. However, some consumers express a dislike for polymer film topsheets and prefer topsheets made of nonwoven materials.

Furthermore, known topsheets typically are not designed specifically for absorption of high viscosity fluids such as runny bowel movements, wound exudates, blood, and menses. As a result, typical topsheets can leak, stain, and contribute to poor skin health due to prolonged contact with the wearer's skin.

Accordingly, there is a need for an improved topsheet for a disposable absorbent article capable of providing for high gush acquisition rates and yet also providing for improved dryness.

Additionally, there is a need an improved topsheet for a disposable absorbent article capable of providing for high gush acquisition rates and yet also providing for improved dryness that is comfortable to the wearer.

Finally, there is a need for a method of relatively inexpensively making a topsheet for a disposable absorbent article capable of providing for high gush acquisition rates and yet also providing for improved dryness.

SUMMARY OF THE INVENTION

An absorbent article having a topsheet, a backsheet, and an absorbent core disposed between the topsheet and the backsheet. The topsheet has a first side and a second side, the first side being a body-facing side. The topsheet defines a CD-MD plane and includes a fibrous nonwoven web and tufts, the tufts having fibers of the fibrous nonwoven web. The topsheet further includes first, second and third zones, each zone being characterized in a Z-direction by the zone fiber orientation, wherein the first and third zones are displaced relative to each other and each include fibers having portions orientated substantially parallel to said CD-MD plane of the topsheet. The second zone is intermediate and adjacent to the first and third zones, the second zone including substantially reoriented fibers that are substantially vertically oriented with respect to the CD-MD plane of said topsheet.

DETAILED DESCRIPTION OF THE INVENTION

Figure 1:
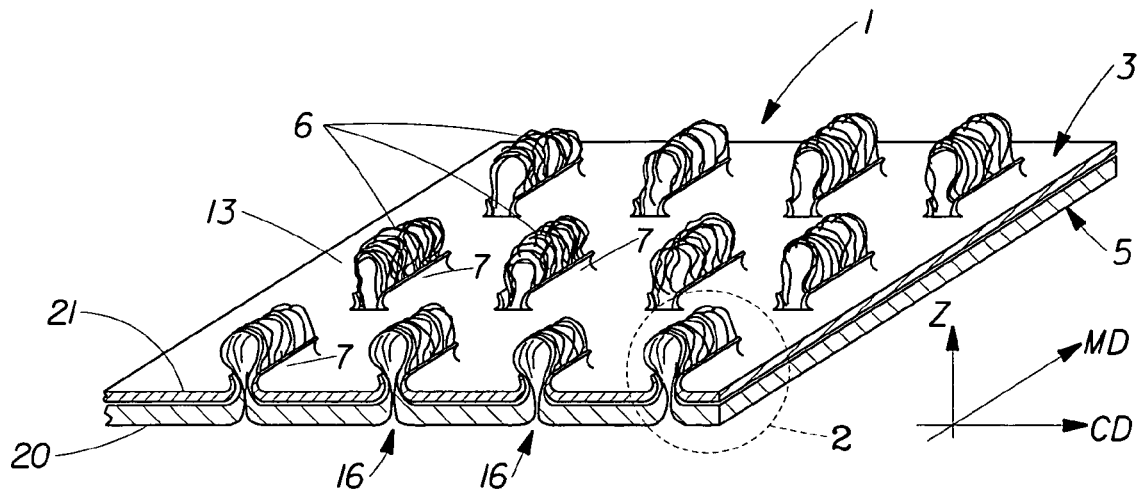
FIG. 1 is a perspective view of a web suitable for use in an article of the present invention.

FIG. 1 shows a laminate web 1 suitable for use in an article of the present invention, hereinafter referred to simply as web 1. Web 1 comprises at least two layers. The layers are referred to herein as generally planar, two-dimensional precursor webs, such as first precursor web 20 and second precursor web 21. Either precursor web can be a film, a nonwoven, or a woven web. Precursor webs 20 and 21 (and any additional webs) can be joined by adhesive, thermal bonding, ultrasonic bonding and the like, but are preferably joined without the use of adhesive or other forms of bonding. As disclosed below, the constituent precursor webs of web 1 can be joined by interlocking mechanical engagement resulting from the formation of tufts 6.

Web 1 has a first side 3 and a second side 5, the term "sides" being used in the common usage of generally planar two-dimensional webs, such as paper and films that have two sides when in a generally flat condition. Each precursor web 20 and 21 has a first surface 12 and 13, respectively, and a second surface 14 and 15, respectively (shown in FIG. 3). Web 1 has a machine direction (MD) and a cross machine direction (CD) as is commonly known in the art of web manufacture. Although the present invention can be practiced with polymer films and woven webs, in a preferred embodiment first precursor web 20 is a nonwoven web comprised of substantially randomly oriented fibers. By "substantially randomly oriented" is meant that, due to processing conditions of the precursor web, there may be a higher amount of fibers oriented in the MD than the CD, or vice-versa. For example, in spunbonding and meltblowing processes continuous strands of fibers are deposited on a support moving in the MD. Despite attempts to make the orientation of the fibers of the spunbond or meltblown nonwoven web truly "random," usually a slightly higher percentage of fibers are oriented in the MD as opposed to the CD. In a preferred embodiment, second precursor web 21 is a nonwoven web similar to the first precursor web 20, or a polymer film, such as a polyethylene film. If desired, the film could be apertured.

Figure 3:
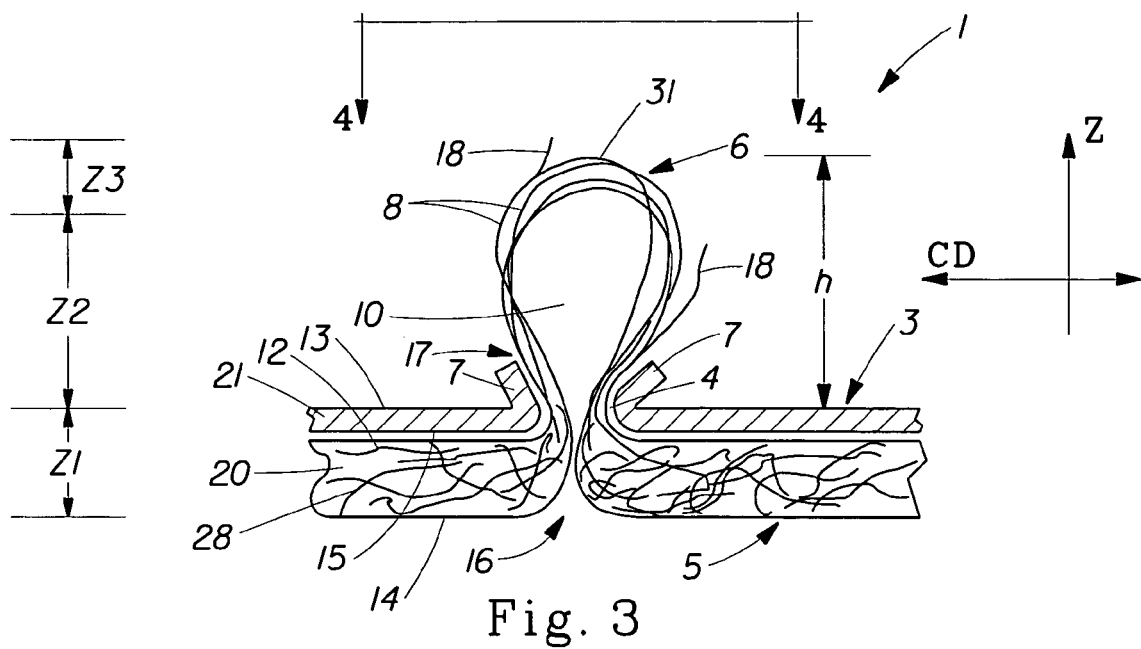
FIG. 3 is a cross-sectional view of section 3-3 of FIG. 2.

In one embodiment, first side 3 of web 1 is defined by exposed portions of the first surface 13 of second precursor web 21 and at least one, but preferably a plurality of, discrete tufts 6 which are integral extensions of the fibers of a nonwoven first precursor web 20. Each tuft 6 can comprise a plurality of looped, aligned fibers 8 extending through second precursor web 21 and outwardly from the first surface 13 thereof. In another embodiment each tuft 6 can comprise a plurality of non-looped fibers 18 (as shown in FIG. 3) that extend outwardly from the first surface 13. In another embodiment, each tuft 6 can comprise a plurality of fibers which are integral extensions of the fibers of both a nonwoven first precursor web 20 and a nonwoven second precursor web 21.

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing processes, spunbonding processes, spunlacing processes, hydroentangling, airlaying, and bonded carded web processes, including carded thermal bonding. The basis weight of nonwoven fabrics is usually expressed in grams per square meter (gsm). The basis weight of the laminate web is the combined basis weight of the constituent layers and any other added components. Fiber diameters are usually expressed in microns; fiber size can also be expressed in denier, which is a unit of weight per length of fiber. The basis weight of laminate webs suitable for use in an article of the present invention can range from 10 gsm to 100 gsm, depending on the ultimate use of the web 1.

The constituent fibers of nonwoven precursor webs 20 and/or 21 can be polymer fibers as known in the art. The fibers can be monocomponent, bicomponent, and/or biconstituent, non-round (e.g., capillary channel fibers), and can have major cross-sectional dimensions (e.g., diameter for round fibers) ranging from 0.1-500 microns. The constituent fibers of the nonwoven precursor webs may also be a mixture of different fiber types, differing in such features as chemistry (e.g. PE and PP), components (mono- and bi-), shape (i.e. capillary channel and round) and the like. The constituent fibers can range from about 0.1 denier to about 100 denier.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the crosssectional area of the fiber and the various polymers are usually not continuous along the entire length of the fiber, instead usually forming fibrils which start and end at random. Biconstituent fibers are sometimes also referred to as multiconstituent fibers.

As used herein, the term "non-round fibers" describes fibers having a non-round cross-section, and include "shaped fibers" and "capillary channel fibers" as are known in the art. Such fibers can be solid or hollow, and they can be tri-lobal, delta-shaped, and are preferably fibers having capillary channels on their outer surfaces. The capillary channels can be of various cross-sectional shapes such as "U-shaped", "H-shaped", "C-shaped" and "V-shaped". One preferred capillary channel fiber is T-401, designated as 4DG fiber available from Fiber Innovation Technologies, Johnson City, Tenn. T-401 fiber is a polyethylene terephthalate (PET).

As used herein, the term "integral" as in "integral extension" when used of the tufts 6 refers to fibers of the tufts 6 having originated from the fibers of the precursor webs 20 and/or 21. Therefore, the looped fibers 8 and non-looped fibers 18 of tufts 6, can be plastically deformed and extended fibers of the first precursor web 20, and are, therefore, integral with first precursor web 20. Similarly, for embodiments wherein second precursor web 21 is a nonwoven comprising similarly extensible fibers, the fibers of second precursor web 21 can contribute to tufts 6. As used herein, "integral" is to be distinguished from fibers introduced to or added to a separate precursor web for the purpose of making tufts, as is commonly done in conventional carpet making, for example.

The number, spacing, and dimensions of tufts 6 can be varied to give varying texture to first side 3 of web 1. For example, if tufts 6 are sufficiently closely spaced the first side 3 of web 1 can have a terry cloth-like feel. Alternatively, tufts 6 can be arranged in patterns such as lines or filled shapes to create portions of a laminate web having greater texture, softness, bulk, absorbency or visual design appeal. For example, when tufts 6 are arranged in a pattern of a line or lines, the tufts can have the appearance of stitching. Tufts 6 can also be arranged to form specific shapes, such as designs, words or logos. Likewise, the size dimensions, such as the height, length and width of individual tufts 6 can be varied. Single tufts can be as long as about 3 cm in length and can be made alone or dispersed among tufts of various sizes.

First precursor web 20 can be a fibrous woven or nonwoven web comprising fibers having sufficient elongation properties to have portions formed into tufts 6. As described more fully below, tufts are formed by urging fibers out-of-plane in the Z-direction at discrete, localized, portions of first precursor web 20. The urging out-of-plane can be due to fiber displacement, i.e., the fiber is able to move relative to other fibers and be "pulled," so to speak, out-of-plane. More often, however, for most nonwoven first precursor webs 20, the urging out-of-plane is due to the fibers of tufts 6 having been at least partially plastically stretched and permanently deformed to form tufts 6. Therefore, in one embodiment, depending on the desired height of tufts 6, the constituent fibers of a nonwoven first precursor webs 20 can exhibit an elongation to break of at least about 5%, more preferably at least about 10%, more preferably at least about 25%, more preferably at least about 50%, and more preferably at least about 100%. Elongation to break can be determined by simple tensile testing, such as by use of Instron tensile testing equipment, and can generally be found on material data sheets from suppliers of such fibers or webs.

It can be appreciated that a suitable nonwoven first precursor web 20 should comprise fibers capable of experiencing sufficient plastic deformation and tensile elongation, or are capable of sufficient fiber mobility, such that looped fibers 8 are formed. However, it is recognized that a certain percentage of fibers urged out of the plane of the first surface 12 of first precursor web 20 will not form a loop, but instead will break and form loose ends. Such fibers are referred to herein as "loose" fibers or "loose fiber ends" 18 as shown in FIG. 3. Loose fiber ends 18 are not necessarily undesirable for the present invention, and in some embodiments, most or all of the fibers of tufts 6 can be loose fiber ends 18. Loose fiber ends 18 can also be the result of forming tufts 6 from nonwoven webs consisting of, or containing, cut staple fibers. In such a case, some number of the staple fiber ends may protrude into the tuft 6, depending upon such things as the number of staple fibers in the web, the staple fiber cut length, and the height of the tufts.

First precursor web 20 can be a fibrous woven or nonwoven web comprising elastic or elastomeric fibers. Elastic or elastomeric fibers can be stretched at least about 50% and return to within 10% of their original dimension. Tufts 6 can be formed from elastic fibers if the fibers are simply displaced due to the mobility of the fiber within the nonwoven, or if the fibers are stretched beyond their elastic limit and are plastically deformed.

For use as a topsheet in the present invention, first precursor web 20 can be relatively hydrophilic compared to second precursor web 21. In a preferred embodiment first precursor web 20 is also hydrophilic compared to the skin of the wearer of an article of the present invention. In this manner, fluid in contact with the topsheet of the present invention can be wetted out onto the fibers of first precursor web, conducted by capillarity action through the openings 4 of the second precursor web 21 to underlying components of an article of the present invention. While actual measures of hydrophilicity or hydrophobicity are not considered to be critical (only relative hydrophilicity/hydrophobicity between the first precursor web 20 and the second precursor web 21), in general, first precursor web 20 can be considered hydrophilic if it exhibits a contact angle with water of less than about 70 degrees. If first precursor web is not naturally hydrophilic (i.e., the polymer properties are not hydrophilic), it can be rendered hydrophilic by methods known in the art, for example, by application of a surfactant to the fibers and/or the web.

Second precursor web 21 can be virtually any web material, the only requirement being that it be less hydrophilic, and even hydrophobic relative to first precursor web 20, and that it have sufficient integrity to be formed into a laminate by the process described below. In one embodiment, second precursor web can be a film or a nonwoven web having sufficiently less elongation properties relative to first precursor web 20, such that upon experiencing the strain of fibers from first precursor web 20 being urged out-of-plane in the direction of second precursor web 21, second precursor web 21 will rupture, e.g., by tearing due to extensional failure, such that portions of first precursor web 20 can extend through, (i.e., "punch through" so to speak), second precursor web 21 to form tufts 6 on first side 3 of web 1, as shown in FIG. 1. In one embodiment second precursor web 21 is a polymer film. In one embodiment second precursor web 21 is a nonwoven web.

Figure 2:
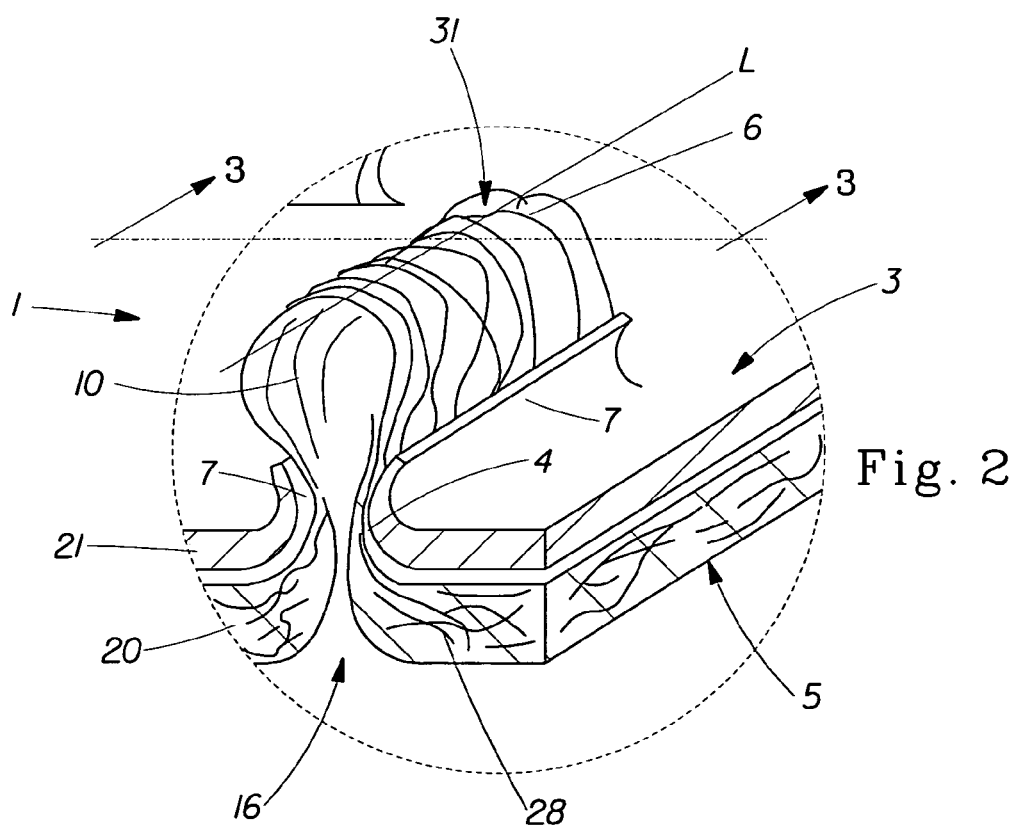
FIG. 2 is an enlarged view of a portion of the web shown in FIG. 1.

A representative tuft 6 for the embodiment of web 1 shown in FIG. 1 is shown in a further enlarged view in FIG. 2. As shown, tuft 6 comprises a plurality of looped fibers 8 that are substantially aligned such that tuft 6 has a distinct linear orientation and a longitudinal axis L. Tuft 6 also have a transverse axis T generally orthogonal to longitudinal axis L in the MD-CD plane. In the embodiment shown in FIGS. 1 and 2, longitudinal axis L is parallel to the MD. In one embodiment, all the spaced apart tufts 6 have generally parallel longitudinal axes L. The number of tufts 6 per unit area of web 1, i.e., the area density of tuft 6, can be varied from 1 tuft per unit area, e.g., square centimeter to as high as 100 tufts per square centimeter. There can be at least 10, or at least 20 tufts 6 per square centimeter, depending on the end use. In general, the area density need not be uniform across the entire area of web 1, but tufts 6 can be only in certain regions of web 1, such as in regions having predetermined shapes, such as lines, stripes, bands, circles, and the like.

As can be appreciated by the description herein, in many embodiments of web 1 openings 4 will have a distinct linear orientation and a longitudinal axis, which is oriented parallel to the longitudinal axis L of its corresponding tuft 6. Likewise, openings 4 will also have a transverse axis generally orthogonal to longitudinal axis in the MD-CD plane.

As shown in FIGS. 1-4, tufts 6 extend through openings 4 in second precursor web 21. Openings 4 are formed by locally rupturing second precursor web 21 by the process described in detail below, or by urging fibers of second precursor web 21 out of plane in like manner as fibers 8. Rupture may involve a simple splitting open of second precursor web 21, such that opening 4 remains a simple two-dimensional aperture. However, for some materials, such as polymer films, portions of second precursor web 21 can be deflected or urged out-of-plane (i.e., the plane of second precursor web 21) to form flap-like structures, referred to herein as flap, or flaps, 7. The form and structure of flaps 7 is highly dependent upon the material properties of second precursor web 21. Flaps 7 can have the general structure of one or more flaps, as shown in FIGS. 1 and 2. In other embodiments, flap 7 can have a more volcano-like structure, as if the tuft 6 is erupting from the flap 7.

In one embodiment flaps 7 do not contribute significantly to the material of tufts 6, and particularly do not contribute significantly to the tactile quality of tufts 6. In one embodiment, therefore, the laminate web 1 comprises at least two layers (i.e., precursor webs 20 and 21), but at least one of the layers (i.e., precursor web 21 in FIGS. 1-4) does not significantly affect on the tactile qualities of tufts 6.

In one embodiment, flaps 7 may extend out of plane significantly, even being as high, so to speak, as the tufts 6 themselves. In this embodiment flaps 7 can cause the tufts 6 to be more resilient and less susceptible to flattening due to compressive or bending forces. In one embodiment, therefore, the laminate web 1 comprises at least two layers (i.e., precursor webs 20 and 21), and both layers affect the tactile qualities of tufts 6.

Tufts 6 can be, in a sense, "punched through" second precursor web 21 and can be "locked" in place by frictional engagement with openings 4. In some embodiments, for example, the lateral width of opening 4 (i.e., the dimension measured parallel to its transverse axis) can be less than the maximum width of the tooth that formed the opening (per the process described below). This indicates a certain amount of recovery at the opening that tends to constrain tuft 6 from pulling back out through opening 4. The frictional engagement of the tufts and openings provides for a laminate web structure having permanent tufting on one side that can be formed without adhesives or thermal bonding.

Tufts 6 can be spaced sufficiently closely so as to effectively cover first side 3 of web 1. In such an embodiment, both sides of web 1 appear to comprise nonwoven fibers integral with first precursor web 20, with a difference between the two sides 3 and 5 being a difference in surface texture. Therefore, in one embodiment, a topsheet of the present invention can be described as a laminate material of two or more precursor webs, wherein both sides of the laminate web are substantially covered by fibers from only one of the precursor webs. Specifically, a topsheet of the present invention can be described as comprising a first relatively hydrophobic component (i.e., second precursor web 21) and a second relatively hydrophilic component (i.e., first precursor web 20) wherein the relatively hydrophilic component extends through the relatively hydrophobic component and is disposed on both sides (i.e., sides 3 and 5) of said topsheet.

As shown in FIGS. 1-4, one characteristic of tufts 6 can be the predominant directional alignment of the fibers 8 or 18. For example, looped, aligned fibers 8 can be described as having a significant or major vector component parallel to the Z-CD plane and the looped fibers 8 have a substantially uniform alignment with respect to transverse axis T when viewed in plan view, such as in FIG. 4. By "looped" fibers 8 is meant fibers 8 that are integral with and begin and end in first precursor web 20 and/or second precursor web 21 but extend outwardly in the Z-direction from first side 3 of web 1. By "aligned" with respect to looped fibers 8 of tufts 6 is meant that looped fibers 8 are all generally oriented such that, if viewed in plan view as in FIG. 4, each of the looped fibers 8 has a significant vector component parallel to the transverse axis T, and preferably a major vector component parallel to the transverse axis T. Although only fibers from first precursor web 20 are shown in FIGS. 1-4, it is to be understood that this is because in these FIGS. a film/nonwoven web 1 is depicted, in which the elongation properties of the web result in tensile failure to form opening 4 through which fibers 8 and/or 18 can protrude. It is understood that if a nonwoven/nonwoven web 1 were depicted, fibers from each of precursor webs 20 and 21 could form tufts 6, and, in such a structure, the tufts 6 could exhibit a substantially layered structure, the fibers of first precursor web 20 being generally internally-disposed in tufts 6.

In contrast, non-looped fibers 18 are integral with, but only begin in first or second precursor webs 20 and/or 21 and have a free end extending outwardly in the Z-direction from first side 3 of web 1. Loose fibers 18 can also have a generally uniform alignment described as having a significant or major vector component parallel to the Z-CD plane.

Figure 4:
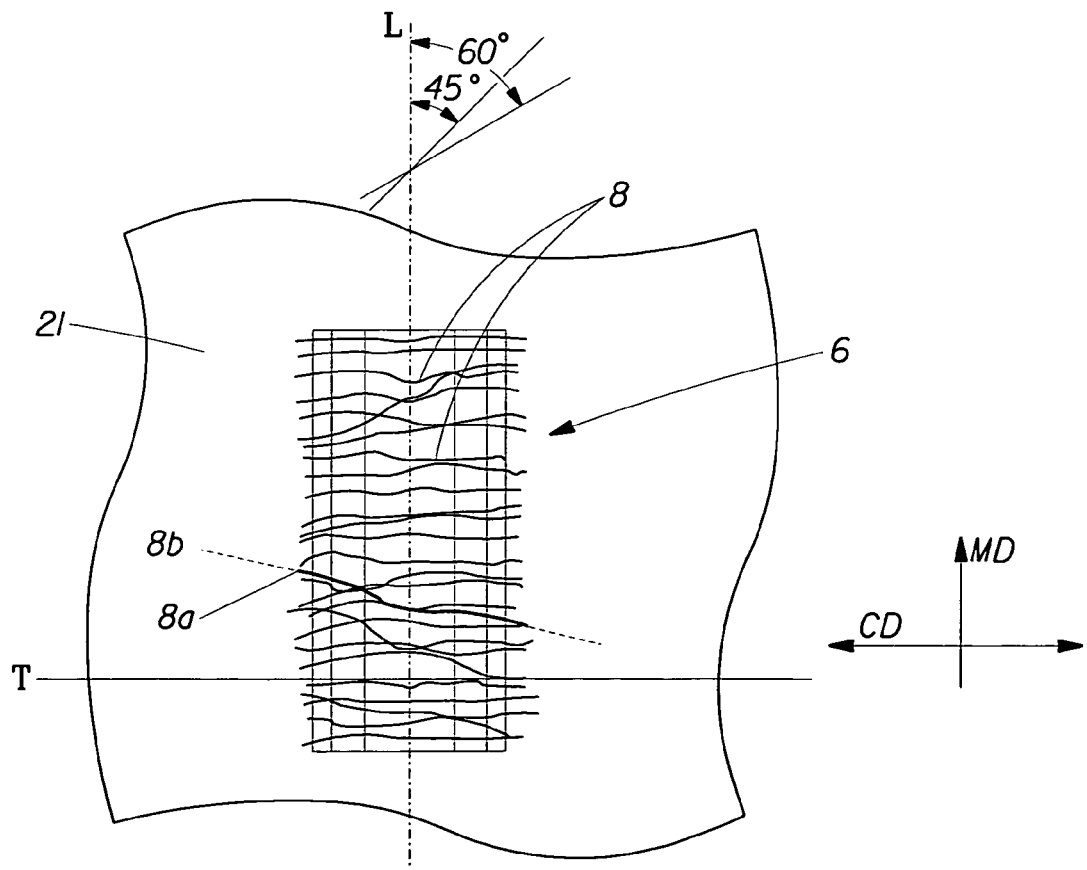
FIG. 4 is a plan view of a portion of the web as indicated by 4-4 in FIG. 3.

For both looped fibers 8 and loose fibers 18, the alignment is a characteristic of tufts 6 prior to any post-manufacture deformation due to winding onto a roll, or compression in use in an article of manufacture. As used herein, a looped fiber 8 oriented at an angle of greater than 45 degrees from the longitudinal axis L when viewed in plan view, as in FIG. 4, has a significant vector component parallel to the transverse axis T. As used herein, a looped fiber 8 oriented at an angle of greater than 60 degrees from longitudinal axis L when viewed in plan view, as in FIG. 4, has a major vector component parallel to the transverse axis T. In a preferred embodiment, at least 50%, more preferably at least 70%, and more preferably at least 90% of fibers 8 of tuft 6 have a significant, and more preferably, a major vector component parallel to transverse axis T. Fiber orientation can be determined by use of magnifying means if necessary, such as a microscope fitted with a suitable measurement scale. In general, for a non-linear segment of fiber viewed in plan view, a straight-line approximation for both longitudinal axis L and the looped fibers 8 can be used for determining the angle of looped fibers 8 from longitudinal axis L. For example, as shown in FIG. 4, one fiber 8a is shown emphasized by a heavy line, and it's linear approximation 8b is shown as a dashed line. This fiber makes an angle of approximately 80 degrees with the longitudinal axis (measured counterclockwise from L).

The orientation of looped fibers 8 in the tufts 6 is to be contrasted with the fiber composition and orientation for first or second precursor webs 20 and 21 (if a nonwoven web is used for second precursor web 21), which, for nonwoven webs is best described as having a substantially randomly-oriented fiber alignment. In a woven web embodiment, the orientation of the looped fibers 8 in tufts 6 could be the same as described above, but the fibers of woven precursor webs would have the orientation associated with the particular weaving process used to make the web, e.g., a square weave pattern.

In the embodiment shown in FIG. 1 the longitudinal axes L of tufts 6 are generally aligned in the MD. Tufts 6 and, therefore, longitudinal axes L, can, in principle, be aligned in any orientation with respect to the MD or CD. Therefore, in general, it can be said that for each tuft 6, the looped aligned fibers 8 are aligned generally orthogonal to the longitudinal axis L such that they have a significant vector component parallel to transverse axis T, and more preferably a major vector component parallel to transverse axis T.

In some embodiments, due to the preferred method of forming tufts 6, as described below, another characteristic of tufts 6 comprising predominantly looped, aligned fibers 8, can be their generally open structure characterized by open void area 10 defined interiorly of tufts 6. By "void area" is not meant an area completely free of any fibers; the term is meant as a general description of the general appearance of tufts 6. Therefore, it may be that in some tufts 6 a loose fiber 18 or a plurality of loose fibers 18 may be present in the void area 10. By "open" void area is meant that the two longitudinal ends of tuft 6 are generally open and free of fibers, such that tuft 6 can form something like a "tunnel" structure in an uncompressed state, as shown in FIG. 3.

Void area 10 is believed to contribute to the surprising fluid handling properties of web 1 when used as a topsheet on a disposable absorbent article, as described more fully below. By having generally open ends tufts 6 provide for "lateral entry" of fluids, particularly viscous fluids having solid components, such as menses.

One way of describing the structure of web 1 is with respect to the three-dimensional fiber orientation in the Z-direction, as shown in FIG. 3, for example. As shown in FIG. 3, at least three "zones" can be identified, with each zone being identified with a portion of web 1 in the Z-direction. A lowermost portion of web 1 designated as zone 1, Z1, extend generally from lower surface 14 of first precursor web 1 to the upper surface 13 of second precursor web 21 and comprises substantially non-reoriented fibers of the first and second precursor webs. The fibers of Z1 are substantially horizontally-oriented with respect to the CD-MD plane with very little Z-directionality. Zone 2, Z2, extends generally from the upper surface 13 of second precursor web 21 to the interior limit of void area 10 and comprises substantially reoriented fibers that are substantially vertically-oriented with respect to the CD-MD plane, that is, fibers in zone Z2 are oriented predominantly in the Z direction and have very little CD or MD directionality. In Zone 3, Z3, which comprises the fibers of distal portion 31 of tuft 6, fibers are again oriented generally horizontally with respect to the CD-MD plane. Therefore, in one embodiment, web 1 can be described structurally as a nonwoven web, which in a generally flat condition defining a plane of the web, the web comprising tufted regions, the tufted regions having three zones, each zone characterized by the zone fiber orientation, wherein the first and third zones comprise fibers having a first orientation substantially parallel to the plane of the web, and a second zone intermediate to and joining the first and third zones, the second zone comprising fibers having second orientation, the second orientation being substantially orthogonal to the first plane of the web, that is, having substantially no portions oriented substantially parallel to the first plane of the web.

In one preferred embodiment of web 1 for use as a topsheet on a disposable article, both precursor webs 20 and 21 are nonwoven webs, with second precursor web 21 being relatively hydrophobic with respect to first precursor web 20 (and, preferably, the skin or hair of the wearer), and both contribute fibers to tufts 6 in a relatively layered manner. In such a topsheet, as described more fully below with respect to FIG. 10, a large portion, if not all, of the fibers in closest proximity to the skin of the wearer can be relatively hydrophobic, such that relatively dry fibers can be in closest proximity to the skin of the wearer. By having lateral entry to the voids 10 of tufts 6, however, fluid can contact relatively hydrophilic fibers of first precursor web 20 and be wicked through web 1 to components, such as a secondary topsheet or absorbent core in the absorbent article.

As a consequence of a preferred method of making web 1, the second side 5 of web 1 exhibits discontinuities 16 characterized by a generally linear indentation defined by formerly random fibers of the second surface 14 of first precursor web 20 having been urged directionally (i.e., in the "Z-direction" generally orthogonal to the MD-CD plane as shown in FIGS. 1 and 3) into tufts 6 by the teeth of the forming structure, described in detail below. The abrupt change of orientation exhibited by the previously randomly-oriented fibers of first precursor web 20 defines the discontinuity 16, which exhibits a linearity such that it can be described as having a longitudinal axis generally parallel to longitudinal axis L of the tuft 6. Due to the nature of many nonwoven webs useful as first precursor webs 20, discontinuity 16 may not be as distinctly noticeable as tufts 6. For this reason, the discontinuities 16 on the second side 5 of web 1 can go unnoticed and may be generally undetected unless web 1 is closely inspected. As such, the second side 5 of web 1 can have the look and feel of an un-tufted first precursor web 20. Thus in some embodiments, web 1 can have the textured look and feel of terry cloth on first side 3, and a relatively smooth, soft look and feel on second side 5, both sides being comprised of fibers from the same nonwoven web, i.e., the first precursor web 20. In other embodiments, discontinuities 16 can appear as apertures, and may be apertures through web 1 via the ends of the tunnel-like tufts 6.

From the description of web 1 comprising at least a nonwoven first precursor web 20, it can be seen that the fibers 8 or 18 of tuft 6 can originate and extend from either the first surface 12 or the second surface 14 of first precursor web 20. Of course the fibers 8 or 18 of tuft 6 can also extend from the interior 28 of first precursor web 20. The fibers 8 or 18 of tufts 6 extend due to having been urged out of the generally two-dimensional plane of first precursor web 20 (i.e., urged in the "Z-direction" as shown in FIG. 3). In general, the fibers 8 or 18 of the tufts 6 comprise fibers that are integral with and extend from the fibers of the either precursor web 20 or 21.

Therefore, from the above description, it is understood that in one embodiment web 1 can be described as being a laminate web formed by selective mechanical deformation of at least a first and second precursor webs, at least the first precursor web being a nonwoven web, the laminate web having a first side, the first side comprising the second precursor web and a plurality of discrete tufts, each of the discrete tufts comprising a plurality of tufted fibers being integral extensions of at least the first precursor web and extending through the second precursor web; and a second side, the second side comprising the first precursor web.

The extension of fibers 8 or 18 can be accompanied by a general reduction in fiber cross sectional dimension (e.g., diameter for round fibers) due to plastic deformation of the fibers and Poisson's ratio effects. Therefore, the aligned looped fibers 8 of tuft 6 can have an average fiber diameter less than the average fiber diameter of the fibers of first or second precursor webs 20 or 21. It is believed that this reduction in fiber diameter contributes to the perceived softness of the first side 3 of web 1, a softness that can be comparable to cotton terry cloth, depending on the material properties of the first precursor web 20. It has been found that the reduction in fiber cross-sectional dimension is greatest intermediate the base 17 and the distal portion 3 of tuft 6. This is believed to be due to the preferred method of making, as disclosed more fully below. Briefly, it is believed that portions of fibers at the base 5 and distal portion 3 of tufts 6 are adjacent the tip of teeth 110 of roll 104, described more fully below, and are frictionally locked and immobile during processing. Thus, the intermediate portions of tufts 6 are more free to stretch, or elongate, and accordingly, can experience a corresponding fiber cross sectional dimension reduction.

Figure 5:
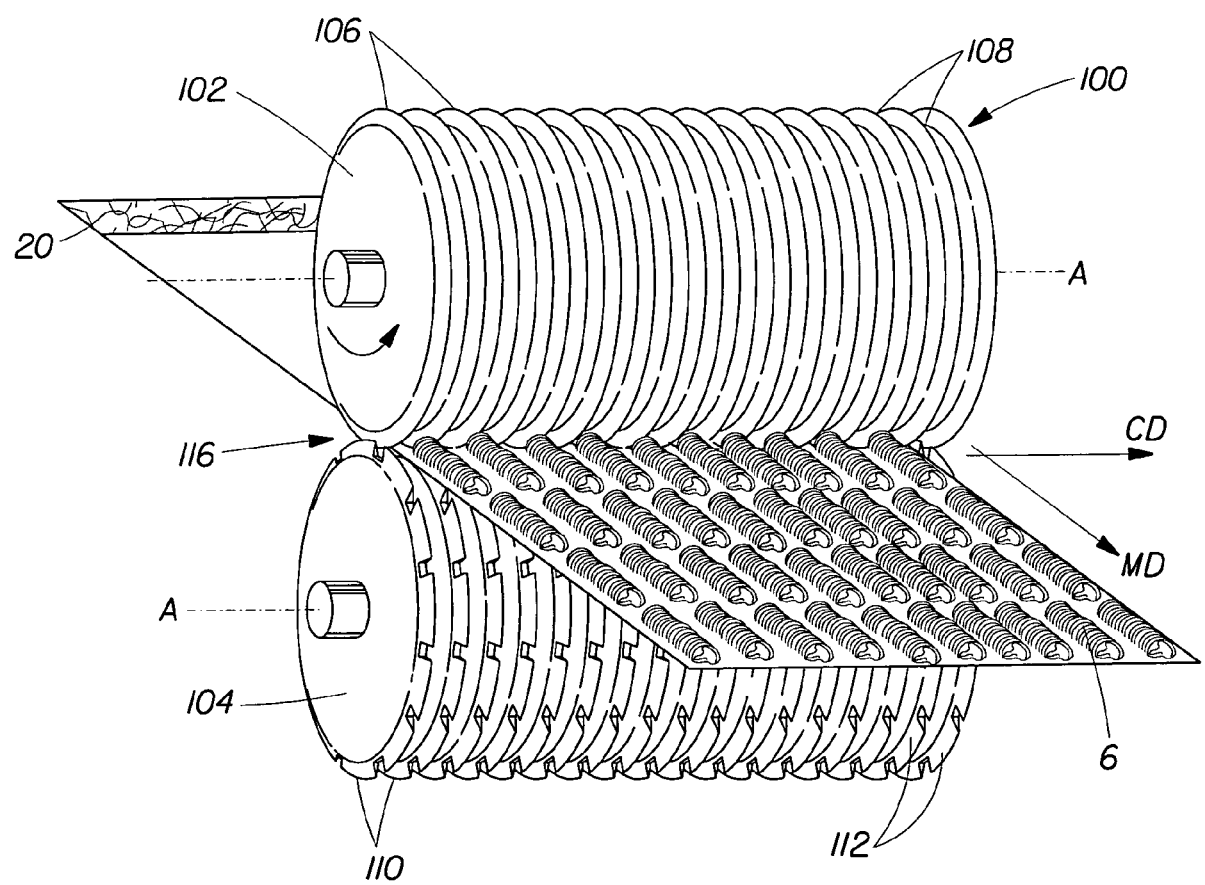
FIG. 5 is a perspective view of an apparatus for forming the web for use in the present invention.

Referring to FIG. 5 there is shown in an apparatus and method for making web 1. The apparatus 100 comprises a pair of intermeshing rolls 102 and 104, each rotating about an axis A, the axes A being parallel in the same plane. Roll 102 comprises a plurality of ridges 106 and corresponding grooves 108 which extend unbroken about the entire circumference of roll 102. Roll 104 is similar to roll 102, but rather than having ridges that extend unbroken about the entire circumference, roll 104 comprises a plurality of rows of circumferentially-extending ridges that have been modified to be rows of circumferentially-spaced teeth 110 that extend in spaced relationship about at least a portion of roll 104. The individual rows of teeth 110 of roll 104 are separated by corresponding grooves 112. In operation, rolls 102 and 104 intermesh such that the ridges 106 of roll 102 extend into the grooves 112 of roll 104 and the teeth 110 of roll 104 extend into the grooves 108 of roll 102. The intermeshing is shown in greater detail in the cross sectional representation of FIG. 6, discussed below. Both or either of rolls 102 and 104 can be heated by means known in the art such as by using hot oil filled rollers or electrically-heated rollers.

In FIG. 5, the apparatus 100 is shown in a preferred configuration having one patterned roll, e.g., roll 104, and one non-patterned grooved roll 102. However, in certain embodiments it may be preferable to use two patterned rolls 104 having either the same or differing patterns, in the same or different corresponding regions of the respective rolls. Such an apparatus can produce webs with tufts 6 protruding from both sides of the web 1.

The method of making a web 1 in a commercially-viable continuous process is depicted in FIG. 5. Web 1 is made by mechanically deforming precursor webs, such as first and second precursor webs, 20 and 21 that can each be described as generally planar and two dimensional prior to processing by the apparatus shown in FIG. 5. By "planar" and "two dimensional" is meant simply that the webs start the process in a generally flat condition relative to the finished web 1 that has distinct, out-of-plane, Z-direction three-dimensionality due to the formation of tufts 6. "Planar" and "two-dimensional" are not meant to imply any particular flatness, smoothness or dimensionality.

The process and apparatus of the present invention is similar in many respects to a process described in U.S. Pat. No. 5,518,801 entitled "Web Materials Exhibiting Elastic-Like Behavior" and referred to in subsequent patent literature as "SELF" webs, which stands for "Structural Elastic-like Film". However, there are significant differences between the apparatus and process of the present invention and the apparatus and process disclosed in the '801 patent, and the differences are apparent in the respective webs produced thereby. As described below, the teeth 110 of roll 104 have a specific geometry associated with the leading and trailing edges that permit the teeth to essentially "punch" through the precursor webs 20, 21 as opposed to, in essence, deforming the web. In a two layer laminate web 1 the teeth 110 urge fibers from precursor webs 20 and 21 out-of-plane by the teeth 110 pushing the fibers 8 through to form tufts 6. Therefore, a web 1 can have tufts 6 comprising loose fiber ends 18 and/or "tunnel-like" tufts 6 of looped, aligned fibers 8 extending away from the surface 13 of side 3, unlike the "tent-like" rib-like elements of SELF webs which each have continuous side walls associated therewith, i.e., a continuous "transition zone," and which do not exhibit interpenetration of one layer through another layer.

Precursor webs 20 and 21 are provided either directly from their respective web making processes or indirectly from supply rolls (neither shown) and moved in the machine direction to the nip 116 of counter-rotating intermeshing rolls 102 and 104. The precursor webs are preferably held in a sufficient web tension so as to enter the nip 16 in a generally flattened condition by means well known in the art of web handling. As each precursor web 20, 21 goes through the nip 116 the teeth 110 of roll 104 which are intermeshed with grooves 108 of roll 102 simultaneously urge portions of precursor webs 20 and 21 out of the plane to form tufts 6. In one embodiment, teeth 110 in effect "push" or "punch" fibers of first precursor web 20 through second precursor web 21. In another embodiment teeth 110 in effect "push" or "punch" fibers of both first and second precursor webs 20 and 21 out of plane to form tufts 6.

As the tip of teeth 110 push through first and second precursor webs 20, 21 the portions of the fibers of first precursor web 20 (and, in some embodiments, second precursor web 21) that are oriented predominantly in the CD across teeth 110 are urged by the teeth 110 out of the plane of first precursor web 20. Fibers can be urged out of plane due to fiber mobility, or they can be urged out of plane by being stretched and/or plastically deformed in the Z-direction. Portions of the precursor webs urged out of plane by teeth 110 result in formation of tufts 6 on first side 3 of web 1. Fibers of precursor webs 20 and 21 that are predominantly oriented generally parallel to the longitudinal axis L, i.e., in the MD as shown in FIG. 1, are simply spread apart by teeth 110 and remain substantially in their original, randomly-oriented condition. This is why the looped fibers 8 can exhibit the unique fiber orientation in embodiments such as the one shown in FIGS. 1-4, which is a high percentage of fibers of each tuft 6 having a significant or major vector component parallel to the transverse axis T of tuft 6.

It can be appreciated by the forgoing description that when web 1 is made by the apparatus and method of the present invention that the precursor webs 20, 21 can possess differing material properties with respect to the ability of the precursor webs to elongate before failure, e.g., failure due to tensile stresses. In one embodiment, a nonwoven first precursor web 20 can have greater fiber mobility and/or greater fiber elongation characteristics relative to second precursor web 21, such that the fibers thereof can move or stretch sufficiently to form tufts 6 while the second precursor web 21 ruptures, i.e., does not stretch to the extent necessary to form tufts. In another embodiment, second precursor web 21 can have greater fiber mobility and/or greater fiber elongation characteristics relative to first precursor web 20, such that both first and second precursor webs 20 and 21 form tufts 6. In another embodiment, second precursor web 21 can have greater fiber mobility and/or greater fiber elongation characteristics relative to first precursor web 20, such that the fibers of second precursor web 21 can move or stretch sufficiently to form tufts 6 while the first precursor web 20 ruptures, i.e., does not stretch to the extent necessary to form tufts.

The degree to which the fibers of nonwoven precursor webs are able to extend out of plane without plastic deformation can depend upon the degree of inter-fiber bonding of the precursor web. For example, if the fibers of a nonwoven precursor web are only very loosely entangled to each other, they will be more able to slip by each other (i.e., to move relative to adjacent fibers by reptation) and therefore be more easily extended out of plane to form tufts. On the other hand, fibers of a nonwoven precursor web that are more strongly bonded, for example by high levels of thermal point bonding, hydroentanglement, or the like, will more likely require greater degrees of plastic deformation in extended out-of-plane tufts. Therefore, in one embodiment, one precursor web 20 or 21 can be a nonwoven web having relatively low inter-fiber bonding, and the other precursor web 20 or 21 can be a nonwoven web having relatively high inter-fiber bonding, such that the fibers of one precursor web can extend out of plane, while the fibers of the other precursor web cannot. Optionally, a precursor web 20 or 21 may have a moderate level of inter-fiber bonding which maximizes the combination of fiber mobility which enables fibers to more easily extend out of the plane to form tufts and web stability which minimizes the collapsing of the tufts.

In one embodiment, for a given maximum strain (e.g., the strain imposed by teeth 110 of apparatus 100), it is beneficial that second precursor web 21 actually fail under the tensile loading produced by the imposed strain. That is, for the tufts 6 comprising only, or primarily, fibers from first precursor web 20 to be disposed on the first side 3 of web 1, second precursor web 21 must have sufficiently low fiber mobility (if any) and/or relatively low elongation-to-break such that it locally (i.e., in the area of strain) fails in tension, thereby producing openings 4 through which tufts 6 can extend.

In another embodiment it is beneficial that second precursor web 21 deform or stretch in the region of induced strain, and does not fail, such that tuft 6 includes portions of second precursor web 21 result.

In one embodiment second precursor web 21 has an elongation to break in the range of 1%-5%. While the actual required elongation to break depends on the strain to be induced to form web 1, it is recognized that for most embodiments, second precursor web 21 can exhibit a web elongation-to-break of 6%, 7%, 8%, 9%, 10%, or more. It is also recognized that actual elongation-to-break can depend on the strain rate, which, for the apparatus shown in FIG. 5 is a function of line speed. Elongation to break of webs used in the present invention can be measured by means known in the art, such as by standard tensile testing methods using standard tensile testing apparatuses, such as those manufactured by Instron, MTS, Thwing-Albert, and the like.

Relative to first precursor web 20, second precursor web 21 can have lower fiber mobility (if any) and/or lower elongation-to-break (i.e., elongation-to-break of individual fibers, or, if a film, elongation-to-break of the film) such that, rather than extending out-of-plane to the extent of the tufts 6, second precursor web 21 fails in tension under the strain produced by the formation of tufts 6, e.g., by the teeth 110 of apparatus 100. In one embodiment, second precursor web 21 exhibits sufficiently low elongation-to-break relative to first precursor web 20 such that flaps 7 of opening 4 only extend slightly out-of-plane, if at all, relative to tufts 6. In general, for embodiments in which tufts 6 comprise primarily fibers from first precursor web 20, it is believed that second precursor web 21 should have an elongation to break of at least 10% less than the first precursor web 20, preferably at least 30% less, more preferably at least 50% less, and even more preferably at least about 100% less than that of first precursor web 20. Relative elongation to break values of webs used in the present invention can be measured by means known in the art, such as by standard tensile testing methods using standard tensile testing apparatuses, such as those manufactured by Instron, MTS, Thwing-Albert, and the like.

In one embodiment second precursor web 21 can comprise substantially all MD-oriented fibers, e.g., tow fibers, such that there are substantially no fibers oriented in the CD. For such an embodiment of web 1 the fibers of second precursor web 21 can simply separate at the opening 4 through which tufts 6 extend. In this embodiment, therefore, second precursor web 21 need not have any minimum elongation to break, since failure or rupture of the material is not the mode of forming opening 4.

The number, spacing, and size of tufts 6 can be varied by changing the number, spacing, and size of teeth 110 and making corresponding dimensional changes as necessary to roll 104 and/or roll 102. This variation, together with the variation possible in precursor webs 20, 21 permits many varied webs 1 having varied fluid handling properties for use in a disposable absorbent article. As described more fully below, a web 1 comprising a nonwoven/film first precursor web/second precursor web combination can also be used as a component in disposable absorbent articles. However, a nonwoven/nonwoven precursor web/second precursor web combination wherein fibers from both webs contribute to tufts 6 is also suitable.

Figure 6:
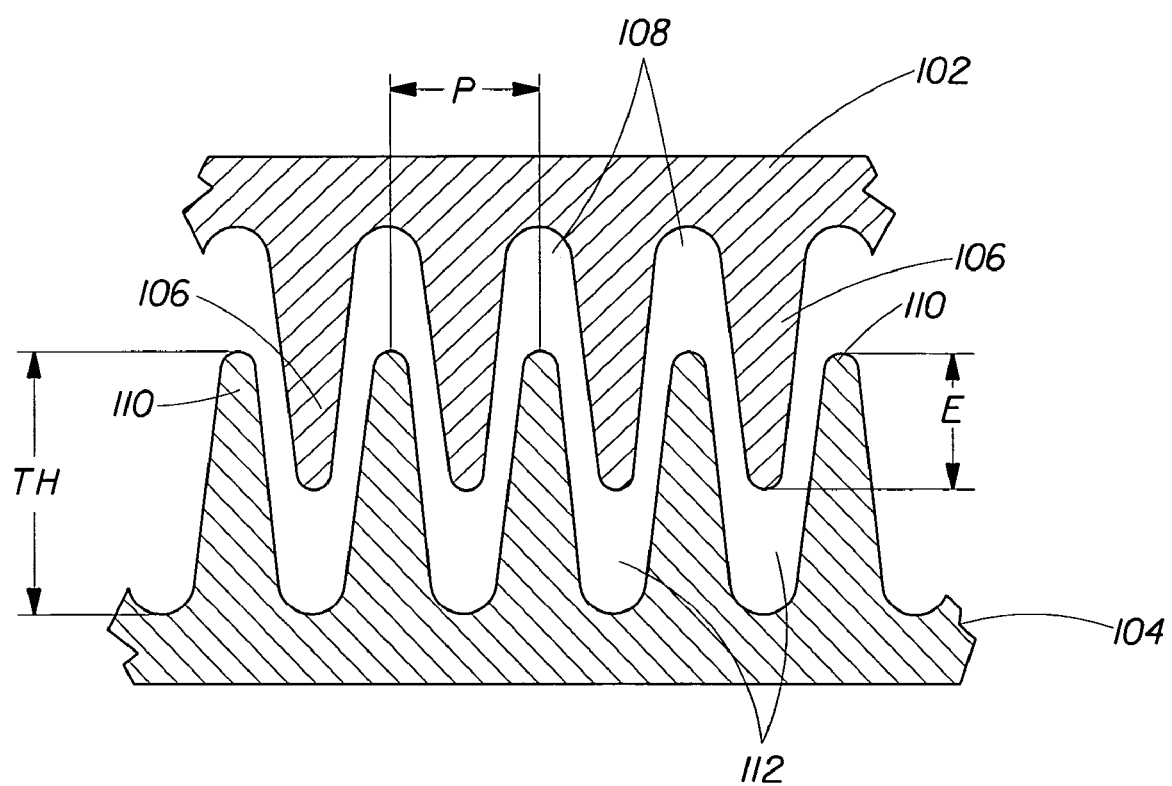
FIG. 6 is a cross-sectional depiction of a portion of the apparatus shown in FIG. 5.

FIG. 6 shows in cross section a portion of the intermeshing rolls 102 and 104 and ridges 106 and teeth 110. As shown teeth 110 have a tooth height TH (note that TH can also be applied to ridge height; in a preferred embodiment tooth height and ridge height are equal), and a tooth-to-tooth spacing (or ridge-to-ridge spacing) referred to as the pitch P. As shown, depth of engagement E is a measure of the level of intermeshing of rolls 102 and 104 and is measured from tip of ridge 106 to tip of tooth 110. The depth of engagement E, tooth height TH, and pitch P can be varied as desired depending on the properties of precursor webs 20, 21 and the desired characteristics of web 1. For example, in general, the greater the level of engagement E, the greater the necessary elongation or fiber-to-fiber mobility characteristics the fibers of portions of the precursor webs intended to form tufts must possess. Also, the greater the density of tufts 6 desired (tufts 6 per unit area of web 1), the smaller the pitch should be, and the smaller the tooth length TL and tooth distance TD should be, as described below.

Figure 7:
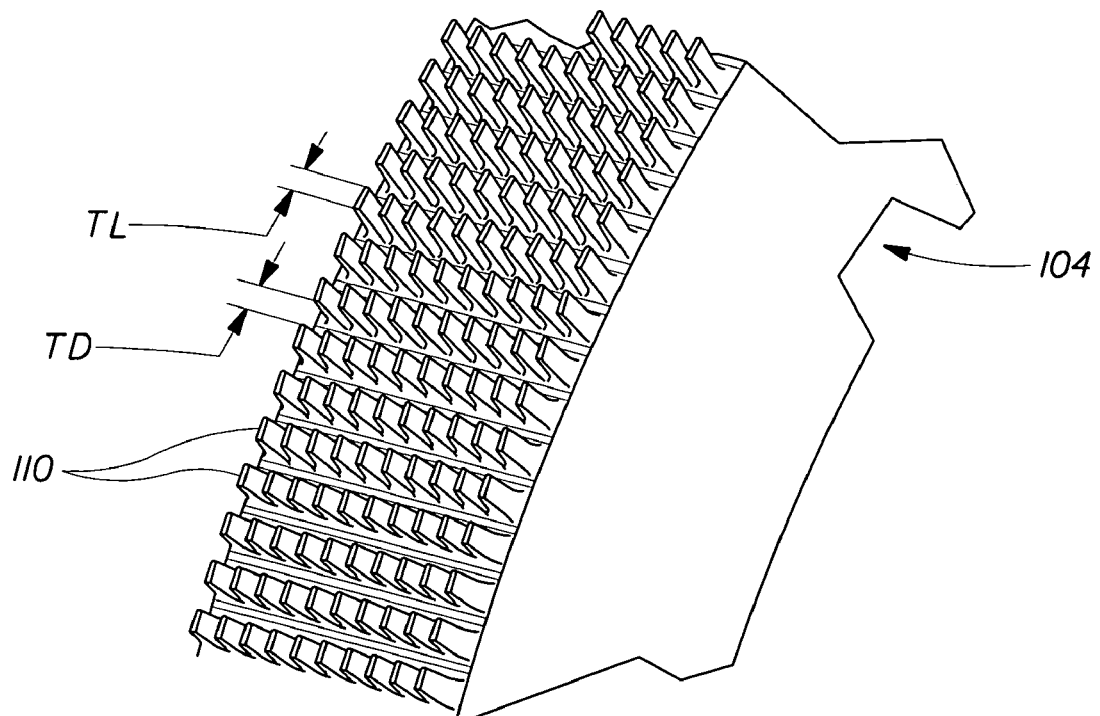
FIG. 7 is a perspective view of a portion of the apparatus for forming one embodiment of a web suitable for use in an article of the present invention.

FIG. 7 shows one embodiment of a roll 104 having a plurality of teeth 110 useful for making a web 1 from a nonwoven first precursor web 20 having a basis weight of between about 60 gsm and 100 gsm, preferably about 80 gsm and a polyolefinic film (e.g., polyethylene or polypropylene) second precursor web 21 having a density of about 0.91-0.94 and a basis weight of about 20 gsm.

Figure 8:
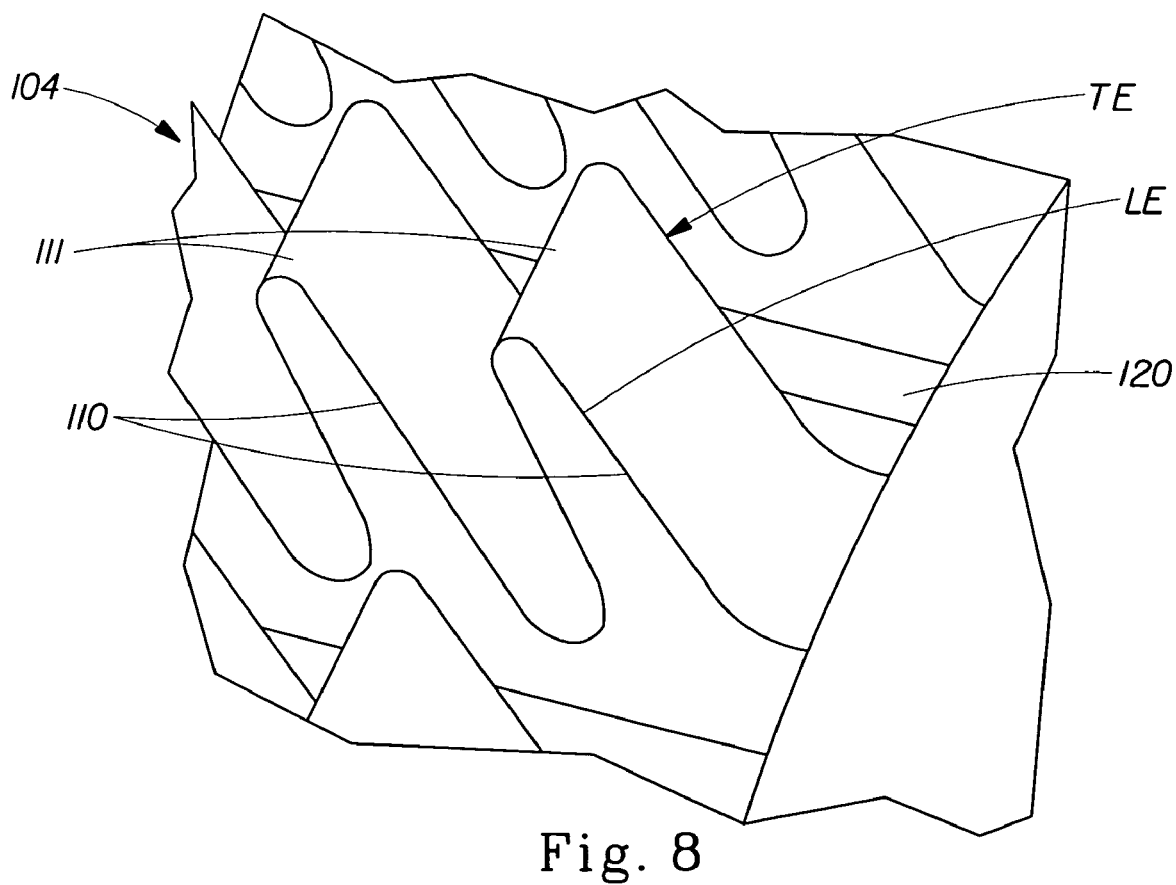
FIG. 8 is an enlarged perspective view of a portion of the apparatus for forming a web suitable for use in an article of the present invention.

An enlarged view of teeth 110 is shown in FIG. 8. In this embodiment of roll 104 teeth 110 have a uniform circumferential length dimension TL measured generally from the leading edge LE to the trailing edge TE at the tooth tip 111 of about 1.25 mm and are uniformly spaced from one another circumferentially by a distance TD of about 1.5 mm. For making a terry-cloth web 1 from web 1 having a total basis weight in the range of about 60 to about 100 gsm, teeth 110 of roll 104 can have a length TL ranging from about 0.5 mm to about 3 mm and a spacing TD from about 0.5 mm to about 3 mm, a tooth height TH ranging from about 0.5 mm to about 5 mm, and a pitch P between about 1 mm (0.040 inches) and about 5 mm (0.200 inches). Depth of engagement E can be from about 0.5 mm to about 5 mm (up to a maximum equal to tooth height TH). Of course, E, P, TH, TD and TL can be varied independently of each other to achieve a desired size, spacing, and area density of tufts 6 (number of tufts 6 per unit area of web 1).

As shown in FIG. 8, each tooth 110 has a tip 111, a leading edge LE and a trailing edge TE. The tooth tip 111 is elongated and has a generally longitudinal orientation, corresponding to the longitudinal axes L of tufts 6 and discontinuities 16. It is believed that to get the tufted, looped tufts 6 of the web 1 that can be described as being terry cloth-like, the LE and TE should be very nearly orthogonal to the local peripheral surface 120 of roll 104. As well, the transition from the tip 111 and LE or TE should be a sharp angle, such as a right angle, having a sufficiently small radius of curvature such that teeth 110 push through second precursor web 21 at the LE and TE. Without being bound by theory, it is believed that having relatively sharply angled tip transitions between the tip of tooth 110 and the LE and TE permits the teeth 110 to punch through precursor webs 20, 21 "cleanly", that is, locally and distinctly, so that the first side 3 of the resulting web 1 can be described as "tufted" rather than "deformed." When so processed, the web 1 is not imparted with any particular elasticity, beyond what the precursor webs 20 and 21 may have possessed originally.

Figure 9:
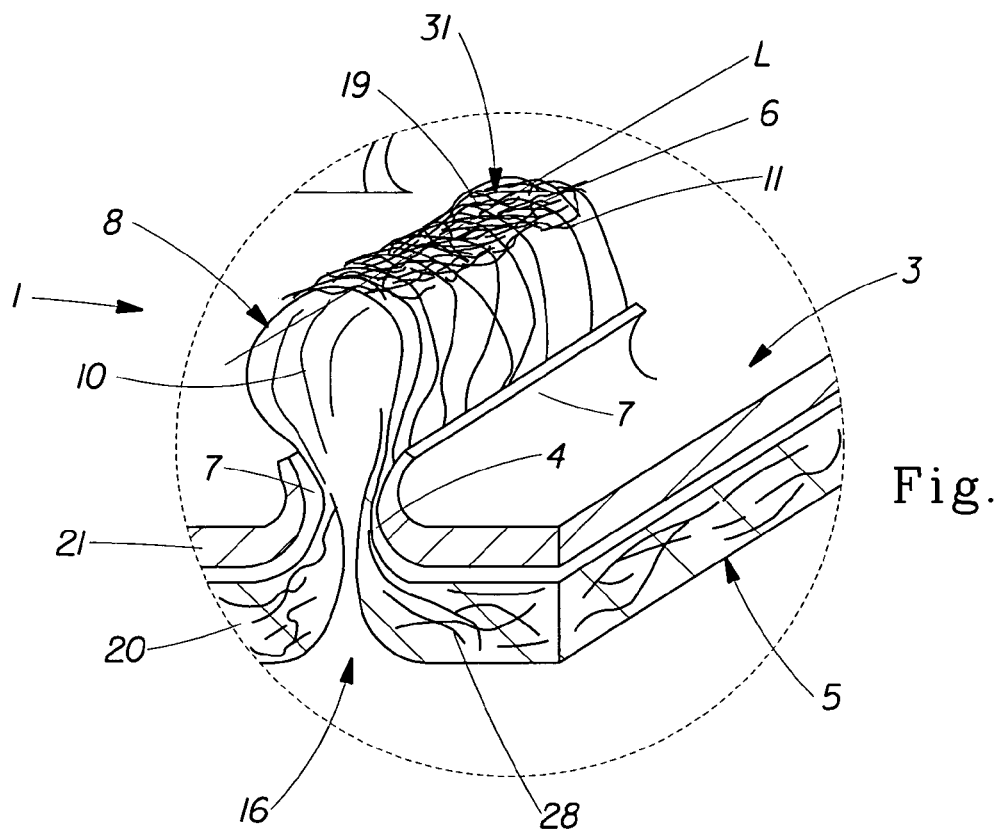
FIG. 9 is an enlarged view of a portion of another embodiment of a web suitable for use in an article of the present invention.

At higher line speeds, i.e., relatively higher rates of processing of the web through the nip of rotating rolls 102 and 104, like materials can exhibit very different structures for tufts 6. The tuft 6 shown in FIG. 9 is similar in structure to the tuft shown in FIG. 2 but exhibits a very different structure, a structure that appears to be typical of spunbond nonwoven first precursor webs 20 processed to form tufts 6 at relatively high speeds, i.e., at high strain rates. Typical of this structure is broken fibers between the proximal portion, i.e., base 7, of tufts 6 and the distal portion, i.e., the top 31, of tuft 6, and what appears to be a "mat" 19 of fibers at the top of the tuft 6. Mat 19 comprises and is supported at the top of tufts 6 by unbroken, looped fibers 8, and also comprises portions of broken fibers 11 that are no longer integral with first precursor web 20. That is, mat 19 comprises fiber portions which were formerly integral with precursor web 20 but which are completely detached from precursor web 20 after processing at sufficiently high line speeds, e.g., 30 meters per minute line speed in the process described with reference to FIG. 5.

Therefore, from the above description, it is understood that in one embodiment web 1 can be described as being a laminate web formed by selective mechanical deformation of at least a first and second precursor webs, at least the first precursor web being a nonwoven web, the laminate web having a first side, the first side comprising the second precursor web and a plurality of discrete tufts, each of the discrete tufts comprising fibers integral with but extending from the first precursor web and fibers neither integral with nor extending from the first precursor web.

Although it is believed that the distinct fiber orientation observed at the distal portion of tufts 6, e.g., mat 19, is due primarily to processing rates, it is also believed to be affected by other parameters, such as fiber type and basis weight of the precursor webs 20 and 21 as well as processing temperatures that can affect the degree of fiber-to-fiber bonding. Matting of fibers is believed to occur on the portion of tuft 6 associated during manufacturing with the tip of tooth 110 of roll 104. It is believed that frictional engagement of the fibers at the tip of the teeth "lock" the fibers in place, thereby limiting fiber elongation and/or fiber mobility, two mechanisms believed to permit formation of tufts 6. Therefore, once locked, so to speak, in position, fibers adjacent tooth 110 tip can be broken, and, due to the random entanglement of the precursor web as well as possible cold welding of fibers due to pressure and friction, the broken fibers 11 become and remain lodged in mat 19 at the distal end 3 of tufts 6.

Precursor webs having relatively higher basis weights generally have relatively more fiber 11 portions in mat 19. In one sense, it appears as if most of the fiber content of the precursor webs in the immediate vicinity of a tooth tip 110 during manufacture can be simply displaced in the Z-direction to the distal portion 3 of tufts 6, resulting in mat 19. First precursor webs 20 comprising relatively low elongation fibers, or fibers with relatively low fiber-to-fiber mobility (e.g., relatively limited capability for fiber reptation) appear to result in relatively few fibers becoming and remaining lodged in mat 19 at the distal end 3 of tufts 6. Fiber-to-fiber mobility can be increased by reducing or eliminating the fiber-to-fiber bonds. Thermal bonds can be completely eliminated (i.e., avoided by not bonding), or reduced in certain nonwoven webs to increase fiber-to-fiber mobility. Similarly, hydroentangled webs can be less entangled to increase fiber-to-fiber mobility. For any precursor web 20, lubricating it prior to processing as disclosed herein can also increase fiber-to-fiber mobility. For example, a mineral oil lubricant can be applied to first precursor web 20 prior to it entering the nip 116 of rolls 102 and 104. Additionally, a plasticizing agent, such as petrolatum, can be added to some synthetic fiber webs, such as polyethylene or a polyethylene and polypropylene web, to increase extensibility.

While not wishing to be bound by theory, it is believed that if the fibers of the first precursor web have a highly curvilinear shape, e.g., curled fibers, the resultant tufts 6 will have more looped fibers 8 and less broken fibers 18 as compared to more linear fiber conformations. It is believed that such fiber conformations have a lesser chance of bridging between two adjacent teeth, and, as a result they are less prone to be stretched beyond their breaking point, and thus have a greater chance of forming complete loop structures. Furthermore, such curvilinear-shaped fibers can be made by using eccentric bicomponent fibers, or side-by-side bicomponent fibers, such as bicomponent fibers consisting of polyethylene and nylon.

It has been found that certain nonwoven webs, such as carded webs comprising staple-length fibers, when used as a precursor web produce very few looped fibers 8 in tufts 6, so that the tufts 6 produced in these webs may not be described as comprising a plurality of looped, aligned fibers 8 as described above with respect to FIGS. 1-4. Instead, carded nonwoven webs can produce tufts 6 having few, if any, looped, aligned fibers 8, and many, if not all, non-aligned fibers and/or broken fibers 18. It is believed that the non-alignment of fibers in tufts 6 made from carded webs is due in part to the nature of the fiber content of carded webs. Staple fibers are not "endless," but, instead have a predetermined length on the order of about 15 mm to about 100 mm, and, more typically from about 40 mm to about 80 mm. Therefore, when a carded web is processed by the apparatus described with respect to FIG. 5, it is believed that there is a much greater likelihood that a loose fiber end will be in the vicinity of a tuft 6 and thus produce a non-looped fiber end in tuft 6. Furthermore, often staple fibers do not have the same elongation characteristics of spunbond or meltblown fibers, for example. However, even if tufts 6 have no looped fibers, the fibrous tufts can nevertheless provide a softness benefit and produce a web useful for use in a disposable absorbent article.

Therefore, from the above description, it is understood that in one embodiment web 1 can be described as being a laminate web formed by selective mechanical deformation of at least a first and second precursor webs, at least the first precursor web being a nonwoven web, the laminate web having a first side, the first side comprising the second precursor web and a plurality of discrete tufts, the tufts comprising a plurality of fibers integral with but extending from said first region.

In preferred embodiments precursor webs are nonwoven web in which there are minimal fiber-to-fiber bonds. For example, the precursor web can be a nonwoven web having a pattern of discrete thermal point bonds, as is commonly known in the art for nonwoven webs. In general, however, it is believed to be desirable to minimize the number of bond points and maximize the spacing so as to allow for some fiber mobility and dislocation at during formation of tufts 6. In general, utilizing fibers having relatively high diameters, and/or relatively high extension to break, and/or relatively moderate or high fiber mobility, results in better and more distinctly formed tufts 6.

Although web 1 is disclosed in preferred embodiments as a two layer web made from two precursor webs, it is not necessary that it be limited to two layers. For example, a three-layer or more laminate can be made from three or more precursor webs, as long as one of the precursor webs can extend out-of-plane to form tufts. In general, it is not necessary that adhesive or other bonding means be utilized to make laminate web 1. The constituent layers of web 1 (e.g., precursor webs 20 and 21 and any other layers) can be held in a face-to-face laminated relationship by virtue of the "locking" effect of the tufts 6 that extend through openings 4 in second precursor web 21. In some embodiments it may be desirable to use adhesives or thermal bonding or other bonding means, depending on the end use application of web 1. For example, a web 1 comprising bicomponent fiber nonwoven webs can be through-air bonded after formation of tufts 6 to provide for layer-to-layer adhesion for greater peel strength and for increased tuft stability. Additionally, it may be desirable to apply adhesive to a portion of one of the precursor webs. For example, in some embodiments adhesive or thermal bonding between layers can be selectively applied to certain regions of web 1. In the case of adhesive application, for example, adhesive can be applied in a continuous manner, such as by slot coating, or in a discontinuous manner, such as by spraying, extruding, and the like. Discontinuous application of adhesive can be in the form of stripes, bands, droplets, and the like.

In a multilayer web 1 each precursor web can have different material properties, thereby providing web 1 with beneficial properties with respect to use as a topsheet in a disposable absorbent article, as described more fully below. For superior fluid handling, for example, first precursor web 20 can be comprised of relatively hydrophilic fibers. Second precursor web 21 can be polymer film, e.g., a polyethylene film or an apertured polyethylene film, and can be hydrophobic or rendered hydrophobic. The tufts 6 of such a web could form an upper layer, i.e., a body-contacting layer when used as a topsheet on a disposable absorbent article. Fluid deposited upon the upper, relatively hydrophilic tufts is quickly transported away from the relatively hydrophobic film to the portion of the first precursor web underlying the second film precursor web layer. One reason for the observed rapid fluid transport is the capillary structures formed by the generally aligned fibers 8, 18 of tufts 6. The fibers 8, 18 form directionally-aligned capillaries between adjacent fibers, and the capillary action is enhanced by the general convergence of fibers near proximal portion 7 of tufts 6.

In another embodiment, first precursor web 20 can be comprised of relatively hydrophilic fibers. Second precursor web 21 can be comprised of fibers that are relatively hydrophobic or rendered hydrophobic (i.e., exhibit a contact angle with water of greater than about 70 degrees). The tufts 6 of such a web could comprise fibers from both precursor webs to form a relatively hydrophobic upper layer, i.e., a body-contacting layer when used as a topsheet on a disposable absorbent article. Fluid deposited upon the web 1 can have lateral entry contact into voids 10 to reach relatively hydrophilic fibers, however, and thereby be quickly transported away to underlying components of the absorbent article. One reason for the observed rapid fluid transport in either structure is believed to be the capillary structures formed by the generally aligned fibers 8, 18 of tufts 6. The fibers 8, 18 form directionally-aligned capillaries between adjacent fibers, and the capillary action is enhanced by the general convergence of fibers near proximal portion 7 of tufts 6.

It is believed that the rapid fluid transport is further increased due to the ability of fluid to enter the web 1 via the voids 10 defined by looped tufts 6. This "lateral entry" capability and/or capillary action, and/or the hydrophilicity gradient afforded by the structure of web 1 makes web 1 an ideal material for optimal fluid handling for disposable absorbent articles. In particular, a multilayer web 1 can provide for even greater improvement in fluid handling characteristics.

In one embodiment, web 1 comprises a nonwoven first precursor web 20 comprising a spunbond nonwoven having a basis weight of about 80 gsm, and comprising polyethylene/polypropylene (sheath/core) bicomponent fibers having an average diameter of about 33 microns, and a second precursor web comprising a polyethylene film having a basis weight of 20 gsm. In this embodiment, web 1 has about 24 tufts 6 per square centimeter, the tufts 6 having a plurality of looped, aligned fibers 8, each of which has an average fiber diameter of about 18 microns. A web of this type can be beneficially used as a topsheet for disposable absorbent articles, as shown below with reference to FIG. 11. For example, such a web 1 is fluid impermeable except in the regions of the tufts 6 which can wick fluid from the first side 3 of web 1 to the second side 5.

Figure 10:
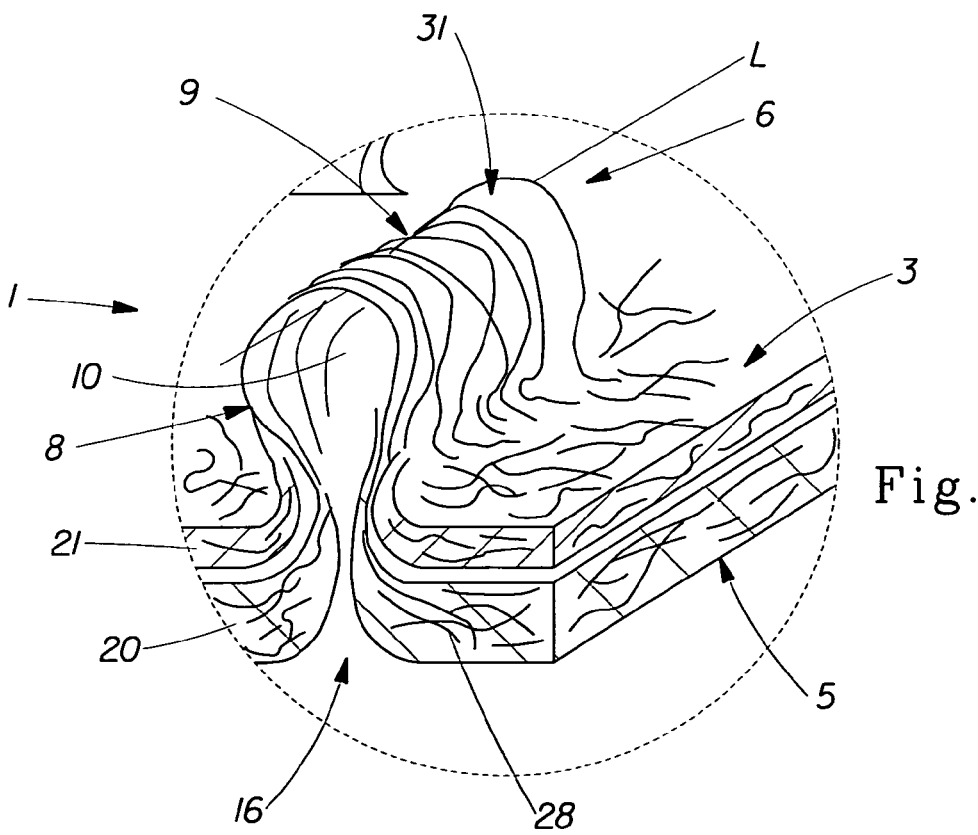
FIG. 10 is an enlarged view of a portion of another embodiment of a web suitable for use in an article of the present invention.

In one embodiment, as depicted schematically in FIG. 10, two nonwoven precursor webs can be used, each precursor web having sufficient fiber mobility or elongation such that tufts 6 comprise fibers from each precursor web. In a most preferred embodiment for use as a topsheet in a sanitary napkin, web 1 can have a relatively hydrophilic first precursor web 20 and a relatively hydrophobic second precursor web 21, such that fibers from the relatively hydrophobic second precursor web 21 extend in the most outwardly extending portions of tufts 6. That is, at the distal portion 31 of tufts 6 there are hydrophobic looped fibers 8 that can form a significant hydrophobic "cap" on the distal portion of the tufts 6. This hydrophobic cap can have significant benefits when web 1 is used as a topsheet in a sanitary napkin. By presenting a substantially fully hydrophobic top surface, i.e., side 3, to the wearer's skin, the topsheet promotes dryness on the skin. However, by presenting lateral entry to underlying hydrophilic fibers 8 in tufts 6 fluid can be quickly wicked through web 1 to underlying components of the sanitary napkin, such as an absorbent core, for example.

Figure 11:
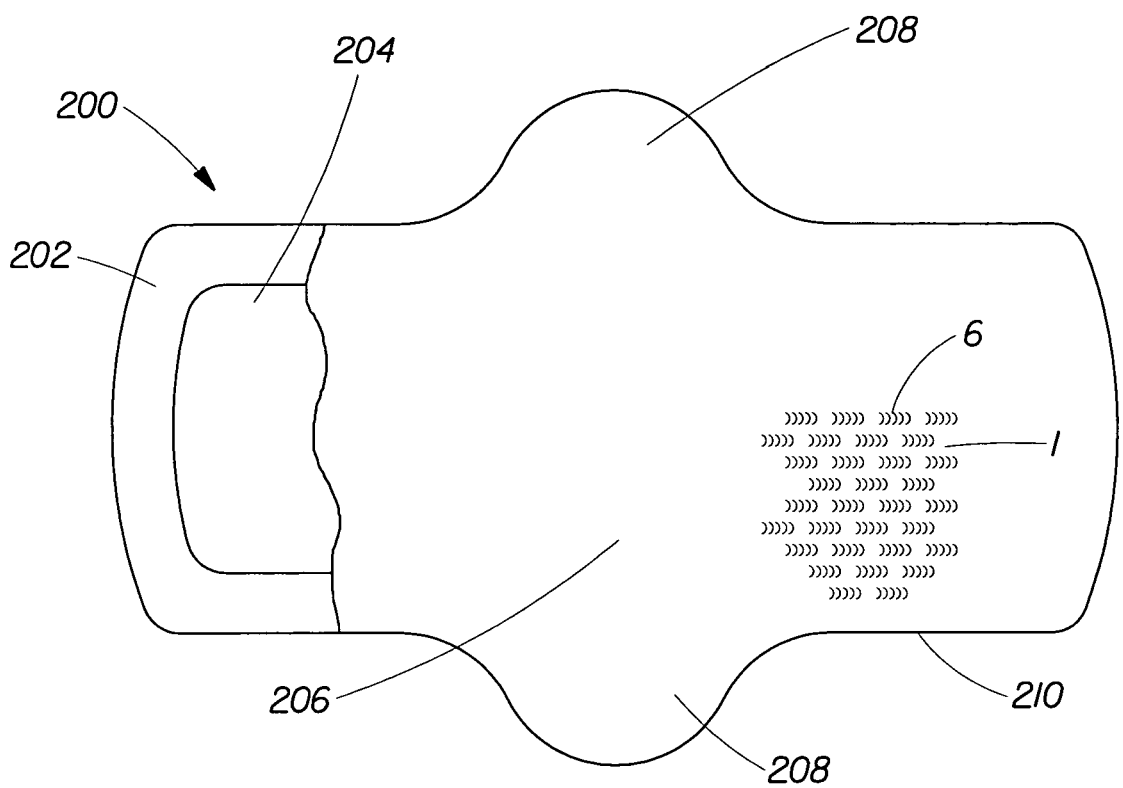
FIG. 11 is a partial cut away plan view of a sanitary napkin of the present invention.

FIG. 11 shows in partial cut away plan view a sanitary napkin having as one of its components a web 1 of the present invention. In general, sanitary napkin 200 comprises a backsheet 202, a topsheet 206 and an absorbent core 204 disposed between the topsheet 206 and backsheet 202 which can be joined about a the periphery 210. Sanitary napkin 1 can have side extensions, commonly referred to as "wings" 208 designed to wrap the sides of the crotch region of the panties of the user of sanitary napkin 1. Sanitary napkins, including topsheets for use as the body facing surface thereof, are well known in the art and need no detailed description of various alternative and optional designs. However, it is noted that web 1 can be used as, or as a component of, one or more of a backsheet, core material, topsheet, secondary topsheet, or wing material.

Web 1 is especially useful as a topsheet 206 of sanitary napkin 200. Web 1 as described with respect to FIG. 10 is particularly beneficial as a topsheet 206 for sanitary napkins due to the combination of excellent fluid gush acquisition and distribution to an underlying absorbent core 204, and excellent prevention of rewet to the body-facing surface of topsheet 206 when in use. As described above, a topsheet 206 comprising a web of the present invention made by using a relatively hydrophilic nonwoven first precursor web 20 and a relatively hydrophobic second precursor web 21 provides for a topsheet 206, that when viewed in plan view as in FIG. 11 presents a substantially hydrophobic body-facing surface. Therefore, in one embodiment, a web 1 useful for a topsheet 206 can be described as a tufted laminate web having two sides, wherein one side projects a substantially hydrophilic surface and the other side projects a substantially hydrophobic surface.

The topsheet 206 can comprise two layers, i.e., one layer corresponding to each precursor web, and the first precursor web could be considered to be a secondary topsheet. But since the two webs are joined into a laminate composite, they are referred to herein as a topsheet 206. The basis weights of the precursor webs can be varied due to cost and benefit considerations. In general, a web 1 having a total basis weight of between about 20 gsm and 100 gsm is desirable for use as a topsheet 206 in a disposable absorbent article, such as a sanitary napkin. Second precursor web 21 can be a nonwoven web or a polymer film web. When made as a hydrophilic/hydrophobic (one web with respect to the other) nonwoven/film laminate, web 1 has been found to combine the softness and fluid capillarity of fiber tufts with the rewet prevention of a fluid impermeable polymer film. Likewise, when made as a hydrophilic/hydrophobic (one web with respect to the other) nonwoven/nonwoven laminate, web 1 has also been found to combine consumer-acceptable softness with excellent gush fluid acquisition and rewet properties.

It is well known in the sanitary napkin field, as illustrated by Table 1 below, and illustrated on the graph of FIG. 16, that there is a tradeoff between improving dryness (i.e., minimizing rewet) and improving gush acquisition rates of menses and other body fluids. That is, in general for known topsheets comprising nonwoven materials, improved dryness can be obtained at the expense of gush acquisition rate. This is believed to be due to the competing fluid handling properties of the nonwoven web. For example, higher density nonwoven webs can improve rewet properties at the expense of gush acquisition rates. Likewise, high surface energy webs can improve gush acquisition rates at the expense of rewet properties. Unexpectedly, with the web of the present invention, these otherwise competing properties are decoupled. For example, for webs having similar capillarity characteristics, increasing the dryness (i.e., reducing rewet) on a topsheet requires that the topsheet be relatively hydrophobic, such that fluid, including menses (although it is recognized that menses has different fluid properties than water) does not wet the surface of the fibers. However, this lack of wettability lowers the gush acquisition rates of fluid into or through the topsheet. Of course, increasing the wettability of the nonwoven fibers to increase the gush acquisition rate has the corresponding effect of increasing the rewet values of the topsheet.

Therefore, when rewet and gush acquisition rate are graphed on orthogonal axes, the data show a very well known and predictable trend showing that as dryness improves, gush acquisition rates decrease. By way of example, the data in Table 1, which is graphed in FIG. 16, was produced using artificial menstrual fluid (AMF) and a test method comparable to the Gush Acquisition Rate and Rewet test method described in the Test Method section below. As shown, current market products fall within a zone generally corresponding to a diagonally extended zone generally from the top left to the bottom right of the graph, as depicted in FIG. 17. However, surprisingly, by use of a web 1 of the present invention as a topsheet 206, some sanitary napkins of the present invention were found to exhibit both acquisition rates and rewet values that lie well above such a diagonal zone, these sanitary napkins showing a marked increase in both dryness and gush acquisition rate.

TABLE 1

| | | AMF Testing of Gush Acquisition and Rewet | | | |
|---|---|---|---|---|---|
| Sample No. | Description | First Precursor Web | Second Precursor Web | Gush Acquisiton Rate (ml/sec) | Rewet (mg) |
| 1 | KOTEX ® Quick Pores | N/A | N/A | 0.33 | 110 |
| 2 | NATURELLA ® | N/A | N/A | 0.30 | 175 |
| 3 | STAYFREE ® | N/A | N/A | 1.07 | 280 |
| 4 | KOTEX LeakLock | N/A | N/A | 0.59 | 138 |
| 5 | Web 1 over ALWAYS ® Maxi Regular Core | PP/Rayon | 25 gsm Bico PE/PP | 0.30 | 147 |
| 6 | Web 1 over ALWAYS ® Maxi Regular Core | 30 gsm hydrophilic BiCo PE/PP | 25 gsm Bico PE/PP | 1.35 | 484 |
| 7 | Web 1 over ALWAYS ® Maxi Regular Core | 30 gsm hydrophilic BiCo PE/PP | 25 gsm PP | 1.64 | 550 |

TABLE 1-continued

AMF Testing of Gush Acquisition and Rewet

| Sample No. | Description | First Precursor Web | Second Precursor Web | Gush Acquisiton Rate (ml/sec) | Rewet (mg) |
|---|---|---|---|---|---|
| 8 | Web 1 over ALWAYS ® Maxi Regular Core | 30 gsm hydrophilic BiCo PE/PP | 25 gsm PP | 0.91 | 369 |
| 9 | Web 1 over ALWAYS ® Maxi Regular Core | 45 gsm 80%/20% 30 denier PET/Co-PET (4DG) | 25 gsm Bico PP/PE | 1.54 | 50 |
| 10 | Web 1 over ALWAYS ® Maxi Regular Core | 46 gsm 80%/20% 6 denier PET/Co-PET (Round) | 25 gsm Bico PE/PP | 1.04 | 55 |
| 11 | Web 1 over ALWAYS ® Maxi Regular Core | 46 gsm 50%/50% 6 denier PET/Co-PET (Round) | 25 gsm Bico PE/PP | 0.51 | 89 |
| 12 | Web 1 over ALWAYS ® Maxi Regular Core | 46 gsm 20%/80% 6 denier PET/Co-PET (Round) | 25 gsm Bico PE/PP | 0.36 | 104 |

Samples 1-4 were all purchased current market products. All values are averages with n=10.

The PP/Rayon nonwovens were a carded blend of 70% 2.2 denier polypropylene(PP)/30% 5 denier rayon, available from PGI Nonwovens under the designation 164-253-6.

The 25 gsm Bico PE/PP nonwovens were relatively hydrophobic spunbond bicomponent PE/PP (sheath/core) fiber nonwoven webs obtained from BBA Nonwovens, Washougal, Wash. under the designation 074YLCO09U.

The hydrophilic BiCo PE/PP was a 30 gsm relatively hydrophobic spunbond bicomponent PE/PP (sheath/core) fiber nonwoven web obtained from BBA Nonwovens, Washougal, Wash. under the designation 088YLCO09U.

The "4DG" fibers were surfactant treated PET, crimped, 2-inch cut length fibers having a cross-section exhibiting channels that can act as fluid capillaries, obtained from Fiber Innovation Technologies, Johnson City, Tenn. Such fibers are sometimes referred to as capillary channel fibers.

The "round" fibers were surfactant treated PET, crimped, 2-inch cut length fibers having a round cross-sectional shape, obtained from Wellman, Inc., Charlotte, N.C. under the designation Type 204.

The "% PET fibers" refers to the percentage of PET fibers in the first precursor web. In all Samples 3-14, these fibers are blended with relatively hydrophilic 6 denier co-PET crimped, 2-inch cut length bicomponent binder fibers (higher melting PET core/low melting point PET sheath) obtained from Kanematsu USA, Gastonia, N.C. under the designation LM651. All percentages refer to weight percent.

Particularly in the Samples using relatively stiff fibers, such as PET fibers, the data showed results heretofore unobtainable, both improved gush acquisition rates, and improved dryness (lowered rewet). Such a surprising finding—both dryness and gush acquisition rate exhibiting a significant directional improvement with the use of the present invention-prompted further testing, this time using a more readily duplicated fluid, namely Paper Industry Fluid, commonly referred to as PIF. PIF is a well-known fluid used for simulating relatively high viscosity fluids such as menses. Additional testing using PWF was performed according to the Gush Acquisition Rate and Rewet method described below. The results of the PIF testing are shown in Tables 2 and 3. Table 2 shows the results of testing the web of the present invention in place of the topsheets on two well-known existing market products. Table 3 shows the results of testing the web of the present invention over current airfelt core of the type used in Always® Maxi Regular sanitary napkins, available from The Procter & Gamble Co., Cincinnati, Ohio.

In general it is noted that certain samples tested with AMF were duplicated using PIF and the results were seen to correlate in a proportional manner, with the PIF giving more modest improvements for both rewet and acquisition rate. That is, for a given sample, testing with PWF shows proportionally poorer values for both dryness and gush acquisition rate than does testing with AMF. However, even with the use of PIF, as shown in Tables 2 and 3, the tested values continue to be better in both gush acquisition rate and rewet than existing products. Therefore, tested values using AMF, menses, and/or consumer experience are each expected to be exhibit better results than those shown in the Tables below.

TABLE 2

PIF Testing Using Current Market Products

| Sample No. | Product | Topsheet | Gush Acquisition Rate (ml/sec) | Gush Acquisition Rate Improvement (%) | Rewet (mg) | Rewet Improvement (%) |
|---|---|---|---|---|---|---|
| 1 | KOTEX® LeakLock | As purchased | 0.39 | | 409 | |
| | | Web of the present invention | 0.67 | 41.8 | 280 | 46.1 |
| 2 | STAYFREE® 4-Wall | As purchased | 0.46 | | 94 | |
| | | Web of the present invention | 0.65 | 28.7 | 49 | 91.8 |

The Samples listed in Table 2 were store-purchased and tested according to the Test Method detailed below. The values shown for Gush Acquisition Rate and Rewet are averages of 10 tests for each value. In the "as purchased" condition, each Sample was tested without modification of the product. As shown in Table 2, for each product additional samples were tested after replacement of the existing topsheet with a web of the present invention as described below. This was accomplished by carefully removing the existing topsheet (and, if necessary any secondary topsheets) so as to not disturb the underlying absorbent core, and thereafter, placing a topsheet of the present invention over the core in a manner to simulate a machine made product. The webs of the present invention used in the testing shown in Table 2 had the following composition:

First precursor web: 45 gsm carded nonwoven web comprising a blend of 80% relatively hydrophilic 30 denier crimped, shaped, 2-inch cut length PET fibers obtained from Fiber Innovation Technologies, Johnson City, Tenn., under the designation 4DG, and 20% relatively hydrophilic 6 denier co-PET crimped, 2-inch cut length bicomponent binder fibers (higher melting PET core/low melting point PET sheath) obtained from Kanematsu USA, Gastonia, N.C. under the designation LM651.

Second precursor web: 30 gsm relatively hydrophobic spunbond bicomponent PE/PP (sheath/core) fiber nonwoven web obtained from BBA Nonwovens, Washougal, Wash. under the designation 088YLCO09U.

The first and second precursor webs were processed by the method described in the specification above using the intermeshing rolls described above. Specifically, for each sample, the toothed rolls had a pitch P of 1.5 mm, an engagement E of 3.4 mm, and a uniform tooth height TH of 3.7 mm. The intermeshing rolls were rotated so as to process the webs at an approximate rate of about 3 m/min.

As shown by the data in Table 2, current market products exhibit a significant improvement in both rewet and acquisition rate by the use of a topsheet comprising a web of the present invention. The measured fluid handling parameters have a direct impact on consumer-desired properties. Therefore, by using topsheets comprising a web of the present invention, current market products can be significantly improved to deliver important consumer benefits.

Additional webs 1 of the present invention were produced with the same second precursor web as those used in Samples 1 and 2 of Table 2, but with varying first precursor web and fiber characteristics, as shown in Table 4. These webs were tested by the Acquisition Rate and Rewet test methods shown below to give the data shown in Table 3. For the data shown in Table 3, each topsheet was tested over airfelt absorbent cores removed from store-bought ALWAYS® Maxi Regular sanitary napkins.

TABLE 3

PIF Testing of Present Invention on ALWAYS® Absorbent Cores

| | First Precursor Web | | | | | |
|---|---|---|---|---|---|---|
| Sample No. | Fiber Size (denier) | PET Fiber Shape | PET Fibers (%) | Web Basis Weight (gsm) | Acquisition Rate (ml/sec) | Rewet (mg) |
| 3 | 6 | 4DG | 80 | 45 | 0.51 | 17.5 |
| 4 | 14 | 4DG | 80 | 45 | 0.64 | 33 |
| 5 | 30 | 4DG | 80 | 45 | 0.44 | 25.7 |
| 6 | 6 | Round | 80 | 45 | 0.11 | 23 |
| 7 | 6 | Trilobal | 80 | 45 | 0.47 | 22 |
| 8 | 6 | 4DG | 80 | 45 | 0.51 | 17.5 |
| 9 | 6 | Round | 80 | 46 | 0.4 | 19.5 |
| 10 | 6 | Round | 80 | 49 | 0.54 | 22 |
| 11 | 6 | Round | 80 | 66 | 0.81 | 27.6 |
| 12 | 30 | 4DG | 20 | 45 | 0.015 | 36.2 |
| 13 | 30 | 4DG | 50 | 45 | 0.33 | 25.3 |
| 14 | 30 | 4DG | 80 | 45 | 0.44 | 25.7 |

Each of the Samples shown in Table 3 were processed with the first precursor web 20 indicated by the method described above using the intermeshing rolls described above. For each sample, the toothed rolls had a pitch P of 1.5 mm, an engagement E of 3.4 mm, and a uniform tooth height TH of 3.7 mm. The intermeshing rolls were rotated so as to process the webs at an approximate rate of about 3 m/min.

The "trilobal" fibers were surfactant treated PET, crimped, 2-inch cut length fibers having a triobal cross-sectional shape obtained from Fiber Innovation Technologies, Johnson City, Tenn.

The "4DG" fibers were surfactant treated PET, crimped, 2-inch cut length fibers having a cross-section exhibiting channels that can act as fluid capillaries, obtained from Fiber Innovation Technologies, Johnson City, Tenn. Such fibers are sometimes referred to as capillary channel fibers.

The "round" fibers were surfactant treated PET, crimped, 2-inch cut length fibers having a round cross-sectional shape, obtained from Wellman, Inc., Charlotte, N.C. under the designation Type 204.

The "% PET fibers" refers to the percentage of PET fibers in the first precursor web. In all Samples 3-14, these fibers are blended with relatively hydrophilic 6 denier co-PET crimped, 2-inch cut length bicomponent binder fibers (higher melting PET core/low melting point PET sheath) obtained from Kanematsu USA, Gastonia, N.C. under the designation LM651. All percentages refer to weight percent.

The web basis weight refers to the basis weight of the first precursor web only.

As can be seen from the Gush Acquisition Rate and Rewet results in Table 3, the web of the present invention provides for superior gush acquisition rates and dryness values compared to other, known topsheets (see, e.g., "as purchased" values in Table 2). On a graph similar to that shown in FIG. 16, this data would be plotted in the upper right quadrant, a clear departure from current, known webs useful as topsheets on disposable absorbent articles.

In particular, from the results in Tables 2 and 3, it can be seen that a web of the present invention, when used as a topsheet in a disposable absorbent article, delivers both a gush acquisition rate of at least 0.11 ml/sec, and a rewet value much less than about 94 mg. In one embodiment a superior disposable absorbent article, such as a sanitary napkin, can be provided by utilizing a topsheet comprising a web of the present invention wherein the article exhibits a rewet value of less than about 75 mg and a fluid acquisition rate of at least about 0.5 ml/sec. In another embodiment, the article can exhibit a rewet value of less than about 25 mg and a fluid acquisition rate of at least about 1.0 ml/sec.

Without being bound by theory, it is believed that the superior fluid handling results can be attributed to at least two factors: (1) the hydrophilicity/hydrophobicity differences between the first and second precursor webs, respectively; and, (2) the presence of relatively stiff fibers in tufts 6 that can aid in retaining caliper under load. That is, relatively stiff fibers oriented generally in the Z-direction (e.g., as shown in FIG. 3) act as flexible columns of support to provide effective stand-off of the web and resistance to compression forces. In one embodiment it is believed to be most beneficial to have relatively stiff fibers in the first precursor web, and relatively soft fibers in the second precursor web, such that upon forming of tufts comprising both fibers from both webs (e.g., as shown in FIG. 10), the relatively soft fibers are at the distalmost portion of the tufts, and therefore, the substantially all the fibers that contact the skin of a wearer can be relatively soft fibers.

Figure 12:
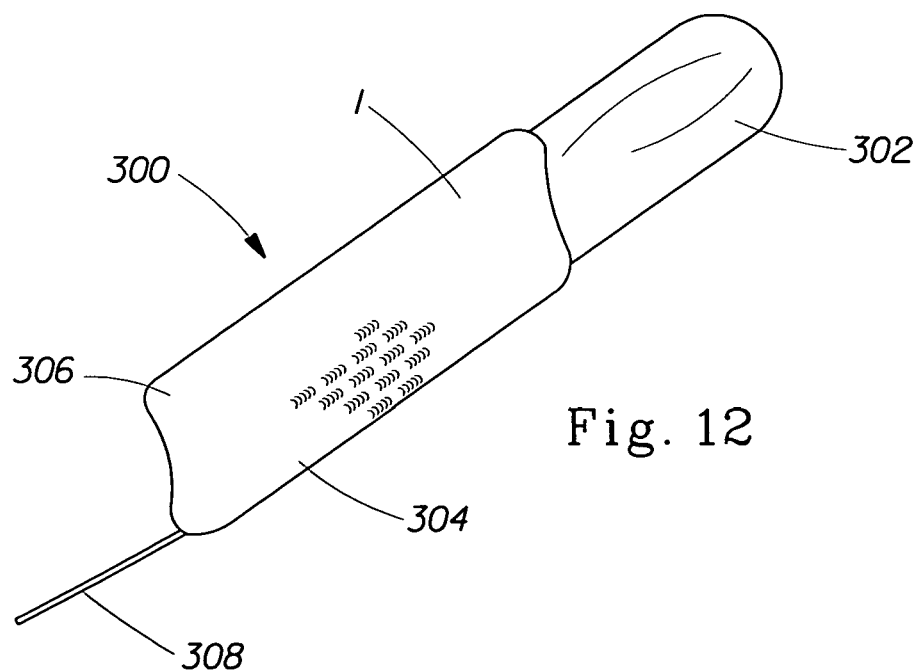
FIG. 12 is a partial cut away perspective view of a tampon of the present invention.

FIG. 12 shows in partial cut away perspective view a catamenial tampon 300 having as one of its components a web 1 of the present invention. In general, tampon 300 comprises a compressed absorbent core 302 and a fluid permeable cover wrap 304 that covers absorbent core 302. Cover wrap 304 may extend beyond one end of absorbent core 302 to form a skirt portion 306. A removal means, such as string 308 can be provided to facilitate removal of the tampon after use. Tampons, including cover wraps for use as the body contacting surface thereof, are well known in the art and need no detailed description of various alternative and optional designs. However, it is noted that web 1 can be used as, or as a component of, one or more of a cover wrap, absorbent core material, or removal means material.

Table 4 below shows representative examples of other structures of webs 1 useful for components in articles of present invention, along with dimensions relative to the apparatus 100 used in the process to make them, as disclosed hereinabove. A brief description of each Sample listed follows Table 4.

TABLE 4

Examples of Apparatus Dimensional Parameters and Web Dimensions

| Sample No. | Precursor Web 1 | Precursor Web 2 | Precursor Web 3 | Pitch (P) <mm> (inches) | Engagement (E) <mm> (inches) | Tooth Height (TH) <mm> (inches) | Loop height (h) (mm) | Avg. Fiber Diameter of Precursor Web 1 (μm) | Avg. Fiber Diameter of Loop Fiber (μm) |
|---|---|---|---|---|---|---|---|---|---|
| 1 | Carded PET nonwoven web | LDPE Film | N/A | <1.5> (0.060) | <3.4> (0.135) | <3.7> (0.145) | 1.59 | 20 | 18 |
| 2 | Spunbond PE/PP core/sheath nonwoven web | 30 lb Kraft paper | N/A | <1.5> (0.060) | <3.4> (0.135) | <3.7> (0.145) | 1.38 | 24 | 13 |
| 3 | Spunbonded PP nonwoven web | Airlaid PET nonwoven web | Spunbonded PP nonwoven web | <1.5> (0.060) | <3.4> (0.135) | <3.7> (0.145) | 1.83 | 34 | 28 |

Figure 13:
FIGS. 13-15 are photomicrographs of a webs suitable for use in an article of the present invention.
Figure 14:
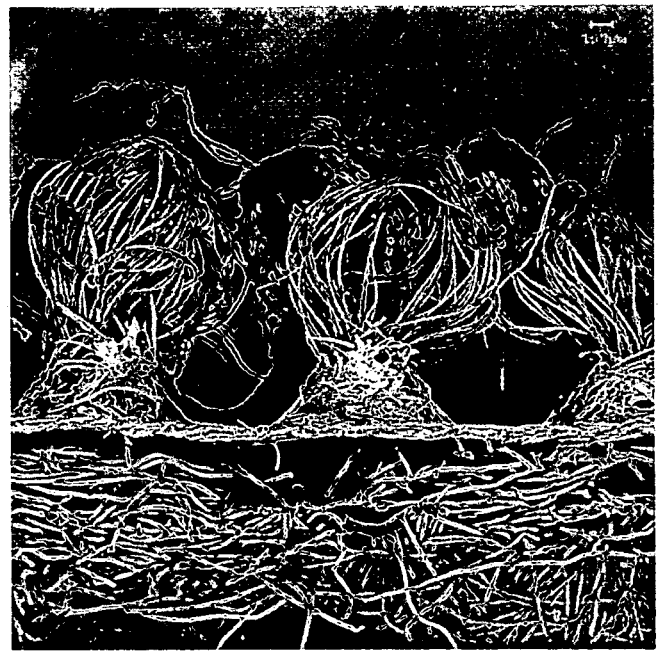

FIG. 13 is a photomicrograph of Sample 1. The first precursor web of Sample 1 was a carded PET nonwoven web having a basis weight of 145 grams per square meter (gsm) that was hand carded from 38 mm (1.5 inch) staple length polyester/co-polyester trilobal-shaped fibers, type F30A, from FIT (Fiber Innovation Technology) Inc., Johnson City, Tenn. The second precursor web of Sample 1 was a low density polyethylene (LDPE) film having a caliper of 0.1 mm (0.004 inch) made by Huntsman Film Products Co., Carrolton Ohio, designated as X420. Sample 1 was produced on an apparatus as described above with respect to FIG. 5 at a line speed of approximately 3 meters per minute (10 feet per minute). As shown in FIG. 13, flap 7 extends significantly out of the plane of the second precursor web (i.e., the film layer) and covers approximately half of the tuft 6. As noted above, this can be desirable where a more stiff, resilient tuft 6 is desired.

Figure 15:
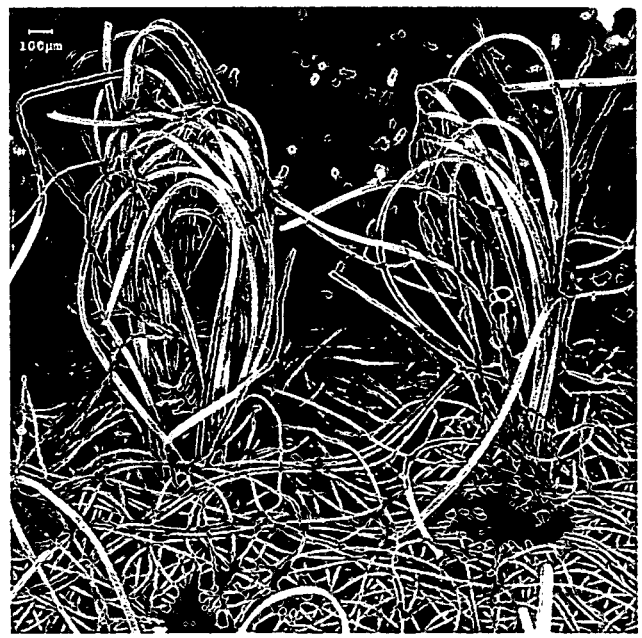

FIG. 15 is a photomicrograph of Sample 2. The first precursor web of Sample 2 is a spunbond PE/PP 50/50 core/sheath nonwoven having a basis weight of 30 gsm and was made by BBA, Simpsonville S.C. The second precursor web of Sample 3 was brown 100% recycled 30 lb Kraft packaging paper available from any source of Kraft paper, e.g., Uline Shipping Supplies, Waukegan, Ill. Sample 2 was produced on an apparatus as described above with respect to FIG. 5 at a line speed of approximately 3 meters per minute (10 feet per minute). As shown in FIG. 15, a second precursor web of Kraft paper can result in openings 4 and flaps 7 that resemble a volcano-shaped opening.

Figure 16:
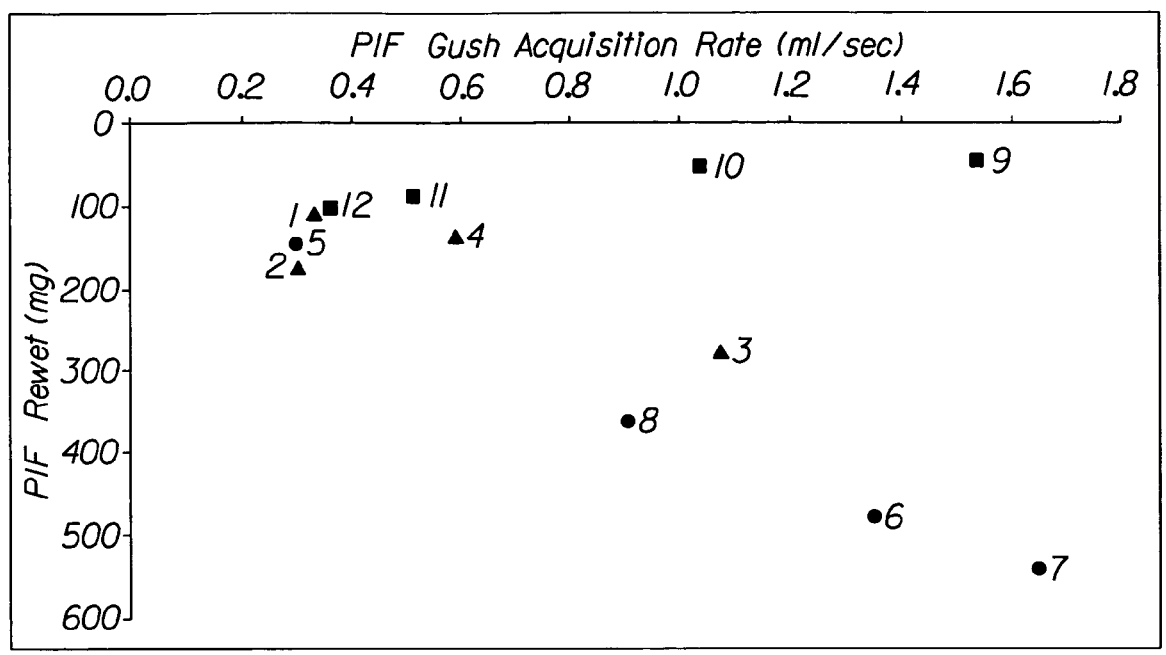
FIG. 16 is a graph of fluid acquisition and rewet data for articles made with webs of the present invention.

FIG. 16 is a photomicrograph of Sample 3, which comprises three precursor webs. The first and third precursor webs of Sample 3 were a spunbond polypropylene nonwoven having a basis weight of 13.5 gsm, designated NW30 from First Quality Nonwovens, Haxleton, Pa. The first and third precursor webs were the outer layers, sandwiching the second precursor web which was a loosely bonded airlaid nonwoven web made from 44 mm (1.75 inch) long staple fibers comprising polyester fibers and PE/PP 50/50 core/sheath nonwoven bicomponent binder fibers in an 80/20 fiber ratio by weight, respectively. The polyester fibers were Type 1311 fibers and the PE/PP fibers were Type 851607 fibers, both fibers being available from FIT (Fiber Innovation Technology) Inc., Johnson City, Tenn. Sample 4 was produced on an apparatus as described above with respect to FIG. 5 at a line speed of approximately 30 meters per minute (100 feet per minute). As shown in FIG. 16, in some embodiments of web 1 there may be no flaps 7 to speak of, but only a slight disruption of second precursor web around the opening through which tufts 6 extend. The tufts 6 shown in FIG. 16 can be seen to comprise two fiber types. Fibers from both the middle, sandwiched airlaid web, and one of the outer layers contribute to the tuft 6.

As can be understood from the above description of webs 1 and apparatus 100 of the present invention, many various structures of webs 1 can be made without departing from the scope of the present invention as claimed in the appended claims. For example, webs 1 can be coated or treated with lotions, medicaments, cleaning fluids, anti-bacterial solutions, emulsions, fragrances, surfactants. In particular, relatively hydrophobic lotion having a hydrophilic/lipophilic balance (HLB) of less than or equal to 7. The lotion can be petrolatum-based and can comprise skin treatment agents and other ingredients as disclosed commonly-assigned U.S. patent application Ser. No. 10/444,241, which is hereby incorporated herein by reference. Web 1 can be treated such that only the distal ends of the tufts 6 have lotion applied thereto, such that the web 1 can be described as a web having a first side and a second side, wherein tufts at least partially originate in the second side and extending to a distal body-facing portion, the distal body-facing portion being relatively hydrophobic with respect to the second side.

Apparatus 100 can be configured to only form tufts 6 on a portion of the web 1, or to form varying sizes or area densities of tufts 6.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Test Method

Preparation of Paper Industry Fluid (PIF)
    Reagents:

| | |
|---|---|
| *Carboxymethylcellulose (CMC), #C-5678 | 15 g |
| *Glycerin #G-7893 | 80 g |
| Sodium Chloride, A.C.S. reagent grade | 10 g |
| Sodium Bicarbonate, A.C.S. reagent grade | 4 g |
| Distilled Water | 1000 mL |
| *[Optional] Indigo Carmine dye, such as Aldrich #13,116-4 | 0.01% |

*Note: available from Sigma Chemical Co. USA (314)771-5750 or Sigma-Aldrich, Germany 49-7329-970.

Procedure:
    Step 1: Add 80.0 (+/−0.05 g) of glycerin to a beaker. Set to one side.
    Step 2: Weigh 15.0 (+/−0.05 g) of CMC.
    Step 3 Slowly add the pre-weighed CMC to the beaker containing the glycerin while continuously stirring using a glass stirring rod. Mix to a slurry (CMC particles suspended in glycerin).
    Step 4: Add 300 mL (+/−5 mL) of distilled water the beaker and continue to mix briefly with the stirring rod. NOTE: Remove any CMC/glycerin residue from the stirring rod by rinsing it off with more distilled water into the beaker using only a small quantity of distilled water (20-50 mL).
    Step 5: Weigh 10.0 (+/−0.01 g) of sodium chloride. Set to one side.
    Step 6: Weigh 4.0 (+/−0.01 g) of sodium bicarbonate. Set to one side.
    Step 7: Place a magnetic stir bar into the beaker of glycerin and place on top of a magnetic stir plate. Turn on the stir plate to continuously mix the solution.
    Step 8: Add all other reagents, and then add more distilled water to the suspension to bring the volume up to approximately 850 mL.
    Step 9: Continue to stir for 20 minutes. Solution should be clear.
    Step 10: Immediately after stirring for 20 minutes, remove the magnetic stir bar and transfer the solution into a volumetric flask. Rinse any remaining residue from the beaker into the solution in the volumetric flask using small quantities of water each time (20-50 mL). Continue to add more distilled water to bring the final volume up to the 1000 mL mark on the flask. The bottom of the meniscus should be level with the etched mark at eye level.
    Step 11: *[Optional] Add 0.01% Indigo Carmine dye.
    Step 12: Place the magnetic stir bar back into the solution in the volumetric flask. Continue to mix for an additional 10-15 minutes.
    Step 13: Using a viscometer check the viscosity of the PIF test fluid at 22+/−0.5 degrees C using a water bath and a thermometer to monitor and control the temperature of the PIF test fluid for the viscosity reading. Follow the viscometer manufacturer's operating instructions for the specific viscometer to be used. Select the appropriate spindle and run at 30 RPM
Note: The density of PIF is 1.03.
Viscosity Target:

Centipoise (cP): Viscosity Range 10-12 cP at 22 degrees C.
Centistokes (cStk): Viscosity Range 9.70-11.64 cStk at 22 degrees C.
Notes: If viscosity is below the target add more CMC. If viscosity is over the target, add more distilled water.
Viscosity of PIF can change with time. Therefore, viscosity measurements must be made daily or prior to use when storing PIF for more than 24 hours.
Discard any unused, or out-of-spec PIF in accord with local/regional safe disposal procedures.
PIF has a shelf life of seven days at room temperature and 14 days refrigerated.

Gush Acquisition and Rewet Test
Step 1: Condition Samples to be tested by equilibrating for 2 hours at a temperature of 69-77 degrees F. and a humidity of 46-54% prior to testing.
Step 2: Samples are to be tested in an environment with a temperature of 69-77 degrees F and a humidity of 46-54%.
Step 3 Place a 4 inch square block with a 1 inch by 0.6 inch opening over the center of the Sample to be tested. Add sufficient weight to the block to achieve a 0.25 psi pressure.
Step 4: Add four 1 mL aliquots of PIF through the opening to the Sample and wait for the each aliquot to absorb into the Sample before adding the next.
Step 5: After the last of the four aliquots of PIF is absorbed into the Sample, wait five minutes and add 3 mL of PIF at a rate of approximately 1 mL/sec to simulate a gush of menses. Time the interval between the first drop of PIF until no PIF is visible on the top surface of the Sample. This time interval is used to calculate and report the gush acquisition rate in ml/sec.
Step 6: Immediately remove the 0.25 psi block and wait 30 seconds, at which time place a stack of seven 5-inch square pre-weighed Ahlstrom Filtration Co. # 632 filter papers (the filter papers also having been pre-conditioned for 2 hours at a temperature of 69-77 degrees F. and a humidity of 46-54% prior to testing) over the central portion of the Sample that received the fluid gush.
Step 7: Place a weight sized to be 0.77 psi on the filter papers for 15 seconds.
Step 8: Remove the 0.77 psi weight and immediately weight the filter papers.
Step 9: Calculate the Rewet in grams by subtracting the weight of the filter paper before being placed under the 0.77 psi weight for 15 seconds from the weight after.
Steps 1-9 are repeated for at least 10 specimens for each Sample, and the average of the 10 specimens is reported.

What is claimed is:

1. An absorbent article comprising a topsheet, a backsheet, and an absorbent core disposed between the topsheet and the backsheet, the topsheet having a first side and a second side, the first side being a body-facing side, said topsheet defining a CD-MD plane and comprising a fibrous nonwoven web and tufts, said tufts comprising fibers of said fibrous nonwoven web and said tufts extending from said nonwoven web, wherein said absorbent core is disposed between said nonwoven web and said backsheet, a plurality of said fibers of said tufts being looped fibers, said topsheet further comprising first, second and third zones, each said zone being characterized in a Z-direction by the zone fiber orientation, wherein said first and third zones are displaced relative to each other and each comprise fibers having portions orientated substantially parallel to said CD-MD plane of said topsheet, and said second zone is intermediate and adjacent to said first and third zones, said second zone comprising substantially reoriented fibers that are substantially vertically oriented with respect to said CD-MD plane of said topsheet, wherein said second zone comprises broken fibers.

2. The absorbent article of claim 1, wherein said topsheet is a laminate of a nonwoven and a film, wherein said tufts extend through said film.

3. The absorbent article of claim 2, wherein said nonwoven web is relatively hydrophilic with respect to said film.

4. The absorbent article of claim 1, wherein said tufts extend out of said fibrous nonwoven web on said first, body-facing side of said topsheet.

5. The absorbent article of claim 1, wherein said tufts are sufficiently closely spaced so as to cover said first, body-facing side of said topsheet.

6. An absorbent article comprising a topsheet, a backsheet, and an absorbent core disposed between the topsheet and the backsheet, the topsheet having a first side and a second side, the first side being a body-facing side and the second side being in fluid communication with the absorbent core, said topsheet defining a CD-MD plane and comprising a fibrous nonwoven web and tufts, said tufts comprising fibers of said fibrous nonwoven web and said tufts extending from said nonwoven web, wherein said absorbent core is disposed between said nonwoven web and said backsheet, a plurality of said fibers of said tufts being looped fibers, said topsheet further comprising first, second and third zones, each said zone being characterized in a Z-direction by the zone fiber orientation, wherein said first and third zones are displaced relative to each other and each comprise fibers having portions orientated substantially parallel to said CD-MD plane of said topsheet, and said second zone is intermediate and adjacent to said first and third zones, said second zone comprising substantially reoriented fibers that are substantially vertically oriented with respect to said CD-MD plane of said topsheet, said tufts at least partially originating in said second side and extending to a distal body-facing portion, the distal body-facing portion being relatively hydrophobic with respect to the second side.

7. The absorbent article of claim 6 wherein said distal body-facing portion of said tufts is rendered hydrophobic by a lotion composition disposed thereon.

8. The absorbent article of claim 7 wherein said lotion composition comprises a hydrophilic/lipophilic balance (HLB) of less than or equal to 7.

9. The absorbent article of claim 7 wherein said lotion composition comprises petrolatum.

10. The absorbent article of claim 6, wherein said topsheet is a laminate of a nonwoven and a film, wherein said tufts extend through said film.

11. The absorbent article of claim 6, wherein said tufts are sufficiently closely spaced so as to cover said first, body-facing side of said topsheet.

12. The absorbent article of claim 2, wherein said film is an apertured polymer film.

13. The absorbent article of claim 10, wherein said film is an apertured polymer film.

14. The absorbent article of claim 1, wherein said tufts have a linear orientation and a longitudinal axis in said CD-MD plane.

15. The absorbent article of claim 1, wherein said tufts are tunnel shaped tufts.

16. The absorbent article of claim 1, wherein said tufts and said fibrous nonwoven web have an average fiber diameter, wherein said average fiber diameter of said tufts is less than said average fiber diameter of said fibrous nonwoven web.

17. The absorbent article of claim 1, wherein said tufts comprise generally aligned fibers.

18. The absorbent article of claim 1, wherein said tufts comprise looped aligned fibers.

19. The absorbent article of claim 6, wherein said tufts have a linear orientation and a longitudinal axis in said CD-MD plane.

20. The absorbent article of claim 6, wherein said tufts are tunnel shaped tufts.

21. The absorbent article of claim 6, wherein said tufts and said fibrous nonwoven web have an average fiber diameter, wherein said average fiber diameter of said tufts is less than said average fiber diameter of said fibrous nonwoven web.

22. The absorbent article of claim 6, wherein said tufts comprise generally aligned fibers.

23. The absorbent article of claim 6, wherein said tufts comprise looped aligned fibers.

* * * * *

UNITED STATES PATENT AND TRADEMARK OFFICE
CERTIFICATE OF CORRECTION

PATENT NO. : 7,670,665 B2
APPLICATION NO. : 11/650821
DATED : March 2, 2010
INVENTOR(S) : Hoying et al.

Page 1 of 1

It is certified that error appears in the above-identified patent and that said Letters Patent is hereby corrected as shown below:

Column 22
Line 43, delete "PWF" and insert --PIF--.
Line 59, delete "PWF" and insert --PIF--.

Signed and Sealed this

Twenty-sixth Day of October, 2010

David J. Kappos
*Director of the United States Patent and Trademark Office*